(12) United States Patent
Ohminami et al.

(10) Patent No.: US 7,873,432 B2
(45) Date of Patent: Jan. 18, 2011

(54) MANUFACTURING INSPECTION/ANALYSIS SYSTEM ANALYZING DEVICE, ANALYZING DEVICE CONTROL PROGRAM, STORAGE MEDIUM STORING ANALYZING DEVICE CONTROL PROGRAM, AND METHOD FOR MANUFACTURING INSPECTION AND ANALYSIS

(75) Inventors: Nobuyuki Ohminami, Fukuyama (JP); Masaru Tanaka, Fukuyama (JP); Takeshi Umemoto, Fukuyama (JP)

(73) Assignee: Sharp Kabushiki Kaisha, Osaka (JP)

( * ) Notice: Subject to any disclaimer, the term of this patent is extended or adjusted under 35 U.S.C. 154(b) by 1351 days.

(21) Appl. No.: 11/369,934

(22) Filed: Mar. 8, 2006

(65) Prior Publication Data
US 2006/0203230 A1 Sep. 14, 2006

(30) Foreign Application Priority Data
Mar. 9, 2005 (JP) ............................. 2005-066336

(51) Int. Cl.
*G06F 19/00* (2006.01)
*G01N 21/00* (2006.01)

(52) U.S. Cl. ................. 700/114; 356/237.1; 356/237.2; 700/121

(58) Field of Classification Search ................. 700/114, 700/121, 110, 95, 90; 356/237.1, 237.2, 356/397
See application file for complete search history.

(56) References Cited

U.S. PATENT DOCUMENTS

| | | | | |
|---|---|---|---|---|
| 5,730,634 A | * | 3/1998 | Seko | 445/3 |
| 5,985,694 A | * | 11/1999 | Cho | 438/108 |
| 6,401,008 B1 | * | 6/2002 | Ehrichs et al. | 700/228 |
| 6,876,445 B2 | * | 4/2005 | Shibuya et al. | 356/237.2 |
| 2004/0021097 A1 | * | 2/2004 | Preece | 250/559.4 |
| 2004/0021856 A1 | * | 2/2004 | Nishiyama et al. | 356/237.2 |
| 2004/0099638 A1 | * | 5/2004 | Miller | 216/94 |
| 2004/0150814 A1 | * | 8/2004 | Yamamoto et al. | 356/237.2 |
| 2005/0095116 A1 | * | 5/2005 | Kitayama | 414/935 |
| 2005/0112889 A1 | * | 5/2005 | Inoue et al. | 438/689 |
| 2006/0146307 A1 | * | 7/2006 | Hansen et al. | 355/67 |
| 2007/0165212 A1 | | 7/2007 | Nishiyama et al. | |

FOREIGN PATENT DOCUMENTS

JP 64-044038 2/1989

(Continued)

*Primary Examiner*—Albert DeCady
*Assistant Examiner*—Jason Lin
(74) *Attorney, Agent, or Firm*—Harness, Dickey & Pierce, P.L.C.

(57) ABSTRACT

A position change section of a processing device changes the position of a treatment object, at the time of performing a process by a process section, to correspond to a predetermined position in conformity to the treatment object. An inspection device inspects the occurrence of a defect on the treatment object having been subjected to processes by a plurality of processing devices. Then an analyzing process for specifying in which processing device the defect occurred is carried out based on (i) positional information of the treatment object, in each of the processing devices, and (ii) defect information defected by the inspection device. With this arrangement, during the process of manufacture of treatment objects, it is possible to precisely specify which processing device or processing device group caused the defect, without performing processes such as attaching, to the treatment object, information regarding processing devices which have conducted processes.

21 Claims, 20 Drawing Sheets

FOREIGN PATENT DOCUMENTS

| | | |
|---|---|---|
| JP | 05-041353 | 2/1993 |
| JP | 2000-200358 | 7/2000 |
| JP | 2000-236006 | 8/2000 |
| JP | 2002-202204 | 7/2002 |
| JP | 2003-166945 | 6/2003 |
| JP | 2004-71671 | 3/2004 |
| JP | 2004-165570 | 6/2004 |
| JP | 2004-304133 | 10/2004 |
| JP | 2005-057029 | 3/2005 |

* cited by examiner

Y-TH PROCESS

Z-TH PROCESS

FIRST PROCESS    SECOND PROCESS

FIRST PROCESS    SECOND PROCESS

FIRST PROCESS    SECOND PROCESS

NORMAL POSITION

NOTCH POSITION CHANGE BY ROTATION

POSITION CHANGE BY HORIZONTAL MOVEMENT

MANUFACTURING INSPECTION/ANALYSIS SYSTEM ANALYZING DEVICE, ANALYZING DEVICE CONTROL PROGRAM, STORAGE MEDIUM STORING ANALYZING DEVICE CONTROL PROGRAM, AND METHOD FOR MANUFACTURING INSPECTION AND ANALYSIS

This Nonprovisional application claims priority under 35 U.S.C. §119(a) on Patent Application No. 066336/2005 filed in Japan on Mar. 9, 2005, the entire contents of which are hereby incorporated by reference.

FIELD OF THE INVENTION

The present invention relates to (i) a manufacturing inspection/analysis system for inspecting a product or a component, which is either in production or finished, (ii) an analyzing device, (iii) an analyzing device control program, (iv) a storage medium storing the analyzing device control program, and (v) a method for manufacturing inspection and analysis.

BACKGROUND OF THE INVENTION

In the manufacture of semiconductor devices or the like, the introduction of foreign matter and the occurrence of a defect in the manufacturing process may cause a fault in the product. It is therefore necessary to quantitatively check the existence of foreign matter and defect, so as to monitor the manufacturing environment. Also, it is necessary to grasp how the foreign matter and defect influence on the yield, and take countermeasures against them in order to improve the yield.

The detection and inspection of the foreign matter and defect are achieved by, for example, a method disclosed in Japanese Laid-Open Patent Application No. 2000-200358 (published on Jul. 18, 2000). This method is performed in the following manner, as shown in FIG. 27. First, in the first step in the manufacturing process, a foreign matter or defect is detected by an automatic appearance inspection device, so that coordinate data of the foreign matter or defect is acquired. In the following second step, a foreign matter or defect is detected by the automatic appearance inspection device in a similar manner, so that coordinate data of the foreign matter or defect is acquired. The sets of coordinate data obtained in the aforesaid two steps are compared with each other. As a result, it is determined where the foreign matter or defect occurs, in the first step or the second step.

A manufacturing device that gives rise to a shape defect is specified by, for example, a method disclosed in Japanese Laid-Open Patent Application No. 5-41353 (published on Feb. 19, 1993). According to this method, as shown in FIG. 28, the manufacturing device is specified in such a manner that, an ID of a manufacturing device having been subjected to the process is patterned on the wafer, as a code pattern, in order to record the history of the manufacturing device that performed the process.

As the circuit pattern of a product is intricate, the detection of a foreign matter and defect becomes difficult. Taking into account this fact, Japanese Laid-Open Patent Application No. 2000-236006 (published on Aug. 29, 2000) discloses such a method that, in order to improve the precision of the defect inspection, a purpose-built monitor wafer is used instead of the inspection of the product itself. According to this method, as shown in FIG. 29, a die pattern is formed on a part of a monitor wafer so that the position of a foreign matter or defect is highly precisely monitored. This improves the precision of the detection of the coordinates of the foreign matter or defect. Moreover, the insufficiency of sensitivity of a product circuit pattern is compensated. Since the distribution of foreign matters and/or defects on a wafer is often peculiar to each type of manufacturing device, the result of the monitoring contributes to the improvement in the devices.

Furthermore, Japanese Laid-Open Patent Application No. 64-44038 (published on Feb. 16, 1989) discloses such a technology that wafers whose positions of the orientation flat faces are different from each other are, by using an wafer setting device, set on a process guiding electrode in a processing chamber of a sheet-feed dry etching device. According to this arrangement, the wafers can be rotated for different angles. Therefore, the positions of the orientation flat faces can be changed and hence the production yield of semiconductor devices is improved.

However, as the size of semiconductor devices reduces, the size of foreign matter and defects that may cause a fault in the product also reduce. This causes such a problem that foreign matters and defects cannot be detected on account of the lack of sensitivity of the appearance inspection device, because the size of the foreign matters and defects is too small.

Even if the appearance inspection device is capable of detecting foreign matters and defects, a time required for the manufacture is lengthened because of a time for the appearance inspection carried out during the manufacturing process. That is to say, in a case where the inspection is performed in each step as illustrated in Japanese Laid-Open Patent Application No. 2000-200358, a time required for the manufacture becomes lengthy. Also, according to the method of Japanese Laid-Open Patent Application No. 2000-200358, the inspection is actually performed after a plurality of steps are carried out, and hence it is difficult to specify which device caused the fault and to specify in which step the fault occurred.

In the method illustrated in Japanese Laid-Open Patent Application No. 5-41353, the ID of the device having been treated is patterned on a wafer. The method therefore has such a problem that the generation of dust on account of the patterning may cause a fault in the product. Moreover, according to the method, the history of treatment is recorded but it is still difficult to specify which device caused a fault.

The method illustrated in Japanese Laid-Open Patent Application No. 2000-236006 requires a purpose-built wafer for detecting foreign matters. Moreover, since the contamination with foreign matters often occurs suddenly, there may be no foreign matters at the time of manufacturing the monitor wafer.

Furthermore, since the purpose of the method disclosed by Japanese Laid-Open Patent Application No. 1-44038 is to prevent unusual electric discharge on account of the uniformly-directed orientation flat faces, the document does not at all disclose a method for specifying which processing device caused a fault.

SUMMARY OF THE INVENTION

The present invention was done in consideration of the above-described problem. The objective of the present invention is to provide: a manufacturing inspection/analysis system that, without performing processes such as attaching, to the treatment object, information regarding processing devices which have conducted processes, makes it possible to properly specify, in the process of manufacture of a treatment object, which processing device or processing device group caused bias in distribution of processing qualities; analyzing device; analyzing device control program, a storage medium storing the analyzing device control program; and a method for manufacturing inspection and analysis.

To achieve this objective, a manufacturing inspection/analysis system includes: processing devices each subjecting at least one treatment object to a predetermined process; an inspection device that detects bias in distribution of processing qualities of said at least one treatment object, after the processing devices perform the process; and an analyzing device that performs an analyzing process so as to specify in which one of the processing devices or one of processing device groups the bias is generated, and at least one of the processing devices including a position change section that changes, at a time of the predetermined process, a position of said at least one treatment object so as to cause the position to correspond to a predetermined position which is in conformity to said at least one treatment object, and the analyzing device including an analyzing process section that carries out the analyzing process in accordance with (i) positional information of said at least one treatment object in each of the processing devices and (ii) processing quality distribution bias information detected by the inspection device.

Also, a manufacturing inspection/analysis method in a manufacturing inspection/analysis system, which includes: processing devices each subjecting at least one treatment object to a predetermined process; an inspection device that detects bias in distribution of processing qualities of said at least one treatment object, after the processing devices perform the process; and an analyzing device that performs an analyzing process so as to specify in which one of the processing devices or each of processing device groups the bias is generated, includes the steps of: (i) in each of the processing devices, changing a position of said at least one treatment object at a time of the predetermined process, in such a manner as to cause the position to correspond to a predetermined position which is in conformity to said at least one treatment object; (ii) by the analyzing device, setting the position determined in the step (i) to be different among the processing devices or processing device groups; and (iii) performing the analyzing process in accordance with (I) positional information of said at least one treatment object in the respective processing devices and (II) processing quality distribution information detected by the inspection device.

According to the arrangement or method above, when the processing device performs a predetermined process, the position of a treatment object is changed in such a manner as to correspond to a predetermined position corresponding to the treatment object. The position change is set so as to be different among the processing devices or processing device groups. On this account, the treatment object or treatment object group, which is subjected to processes in the respective processing devices or processing device groups, is at different positions in the respective processing devices or processing device groups.

Meanwhile, in a case where bias in distribution of processing qualities is generated on the treatment object on account of a process by a processing device, the bias is likely to be peculiar to that processing device. Therefore, as the aforesaid arrangement and method describe, it is possible to specify which processing device or processing device group caused the bias, in reference to (i) positional information of the treatment object in each of the processing devices and (ii) processing quality distribution bias information detected by the inspection device.

In other words, the above-described arrangement and method make it possible to properly specify, in the process of manufacture of the treatment object, which processing device or processing device group caused the bias, without performing processes such as attaching, to the treatment object, information regarding processing devices which have conducted processes.

It is noted that the bias in distribution of processing qualities is, for example, a defect or a change in the processing qualities.

Additional objects, features, and strengths of the present invention will be made clear by the description below. Further, the advantages of the present invention will be evident from the following explanation in reference to the drawings.

DESCRIPTION OF THE EMBODIMENTS

The following will describe an embodiment of the present invention.

(Manufacturing Inspection/Analysis System)

Figure 2:
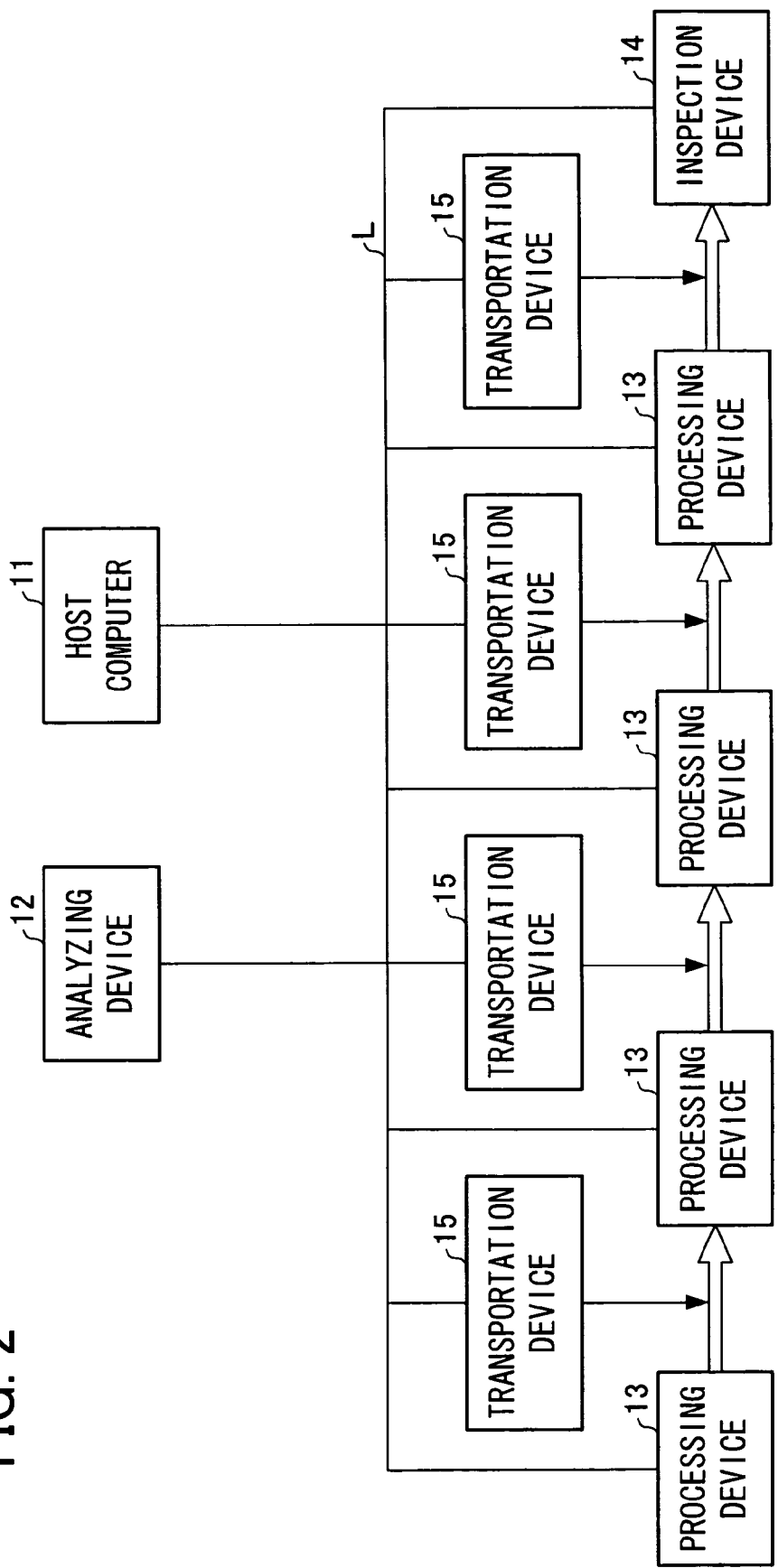
FIG. 2 is a block diagram illustrating an outline of the manufacturing inspection/analysis system.

FIG. 2 is a block diagram that outlines a manufacturing inspection/analysis system of the present embodiment. As shown in the figure, the manufacturing inspection/analysis system includes a host computer 11, an analyzing device 12, processing devices 13, an inspection device 14, and transportation devices 15. The host computer 11, analyzing device 12, processing devices 13, inspection devices 14, and transportation devices 15 are connected with each other via a LAN (Local Area Network) L, so as to be capable of communicating with each other. The LAN L may be wired or wireless. The communication between the devices may be performed by a communication system other than the LAN.

The host computer is a main computer that performs the overall control of the manufacturing inspection/analysis system. The analyzing device 12 performs a defect analysis process which is described below. The processing devices 13 perform, for example, respective processes of manufacturing a treatment object such as a semiconductor wafer. Example of the processing devices 13 include a film forming device, heat treatment device, injection device, etching device, polishing device, applicator device, exposing device, developing device, washing device, cutting device, adhesion device, joining device, film thickness measurement device, line width measurement device, and alignment checking device.

The inspection device 14 inspects if a defect occurs in the treatment object, after the processes performed by the processing devices 13 are completed. The transportation devices 15 transport the treatment object from one processing device 13 to another processing device 13 that carries out the next process.

(Analyzing Device, Processing Devices, Inspection Device)

Figure 1:
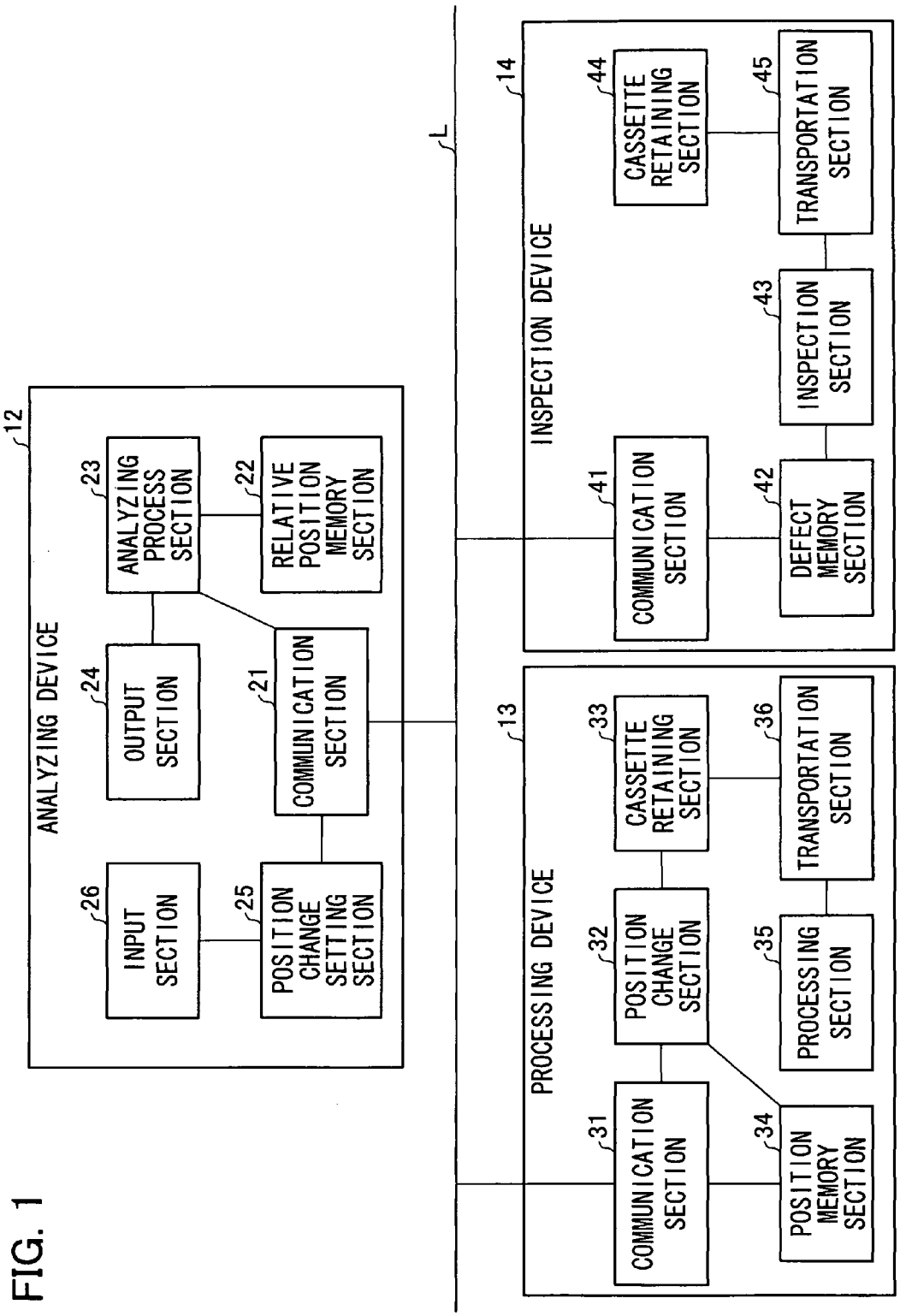
FIG. 1 is a block diagram illustrating an outline of an analyzing device, processing device, and inspection device, which are provided in a manufacturing inspection/analysis system of an embodiment of the present invention.

FIG. 1 is a block diagram showing the analyzing device 12, processing devices 13, and inspection device 14 in detail.

(Analyzing Device)

The analyzing device 12 includes a communication section 21, a relative position memory section 22, an analyzing process section 23, an output section 24, a position change setting section 25, and an input section 26. The communication section 21 is a communication interface for communicating with the host computer 11, processing devices 13, and inspection device 14, via the LAN L.

The analyzing process section 23 performs the analyzing process so as to specify in which processing device 13 a defect occurs, in reference to (i) positional information of the treatment object, which is supplied from the processing devices 13 and (ii) positional information of the occurrence of a defect, which is supplied from the inspection device 14. The details of this analyzing process will be described later. The relative position memory section 22 memorizes the relative positional relationship between the position where the defect of the treatment object occurs and the position where the treatment object locates in a particular process, in reference to (i) the positional information of the treatment object, which is supplied from the processing devices 13 and (ii) the positional information of the occurrence of a defect, which is supplied from the inspection device 14. This memorizing process is carried out by the analyzing process section 23. The output section 24 outputs the result of the analyzing process performed by the analyzing process section 23. The output section 24 includes, for example, display means or printing means.

The input section 26 receives various input instructions which are inputted by an operator into the analyzing device 12. The position change setting section 25 sets in what manner the treatment object is positioned in each of the processing devices, in reference to the information regarding the processing devices 13 used for the manufacture, which information is inputted using the input section 26.

Instead of receiving the input by the operator via the input section 26, the position change setting section 25 may receive, from the host computer 11 for example, information regarding the processing devices 13 used for the manufacture, so as to perform the process. Also, in a case where the position of the treatment object has already been set in each processing device 13, the input section 26 and/or the position change setting section 25 may not be provided.

(Processing Devices)

Each of the processing devices 13 includes a communication section 31, a position change section 32, a cassette retaining section 33, a position memory section 34, a processing section 35, and a transportation section 36. The communication section 31 is a communication interface for communicating with the host computer 11 and analyzing device 12, via the LAN L.

The cassette retaining section 33 retains a cassette (treatment object transportation member) that houses a plurality of treatment objects transported by the transportation device 15. The transportation section 36 transports the treatment object from the cassette retained by the cassette retaining section 33 to the processing section 35. The processing section 35 actually subjects the treatment object to the process of the processing device 13.

The position change section 32 changes the orientation of the treatment object stored in the cassette retained by the cassette retaining section 33. The orientation change is carried out based on the information which is supplied to the communication section 31 and is set by the position change setting section 25 of the analyzing device 12. The position memory section 34 memorizes the positional information of each treatment object having been subjected to the process, after the orientation of each object is changed by the position change section 32. The positional information is supplied to the analyzing device 12 via the communication section 31.

In the example above, after the orientation of the treatment object stored in the cassette retained by the cassette retaining section 33 is changed by the position change section 32, the treatment object is transported to the processing section 35. In a case where the position of the treatment object can be changed in the processing section 35, the position change section 32 changes the position in the processing section 35. Also, the treatment objects may not be transported together in the cassette but transported one by one.

The position memory section 34 may be provided on the analyzing device 12 side, instead of being provided in the processing device 13. In this case, the positional information outputted from the position change section 32 is supplied, via the LAN L, to the position memory section 34 on the analyzing device 12 side, and is stored therein.

(Inspection Device)

The inspection device 14 includes a communication section 41, a defect memory section 42, an inspection section 43, a cassette retaining section 44, and a transportation section 45. The communication section 41 is a communication interface for communicating with a host computer 11 and an analyzing device 12, via a LAN L.

The cassette retaining section 44 retains a cassette including treatment objects transported by the transportation device 15. The transportation section 45 transports the treatment object from the cassette retaining section 44, where the treatment object is stored, to the inspection section 43. The inspection section 43 inspects a defect occurring on the treatment object.

The defect memory section 42 memorizes defect information regarding each treatment object inspected by the inspection section 43. The defect information is supplied to the analyzing device 12 via the communication section 41.

The defect memory section 42 may be provided on the analyzing device 12 side, instead of the inside of the inspection device 14. In this case, the defect information outputted from the inspection section 43 is supplied via the LAN L, and memorized in the defect memory section 42 on the analyzing device 12 side.

(Specific Example of Inspection Device)

Figure 3:
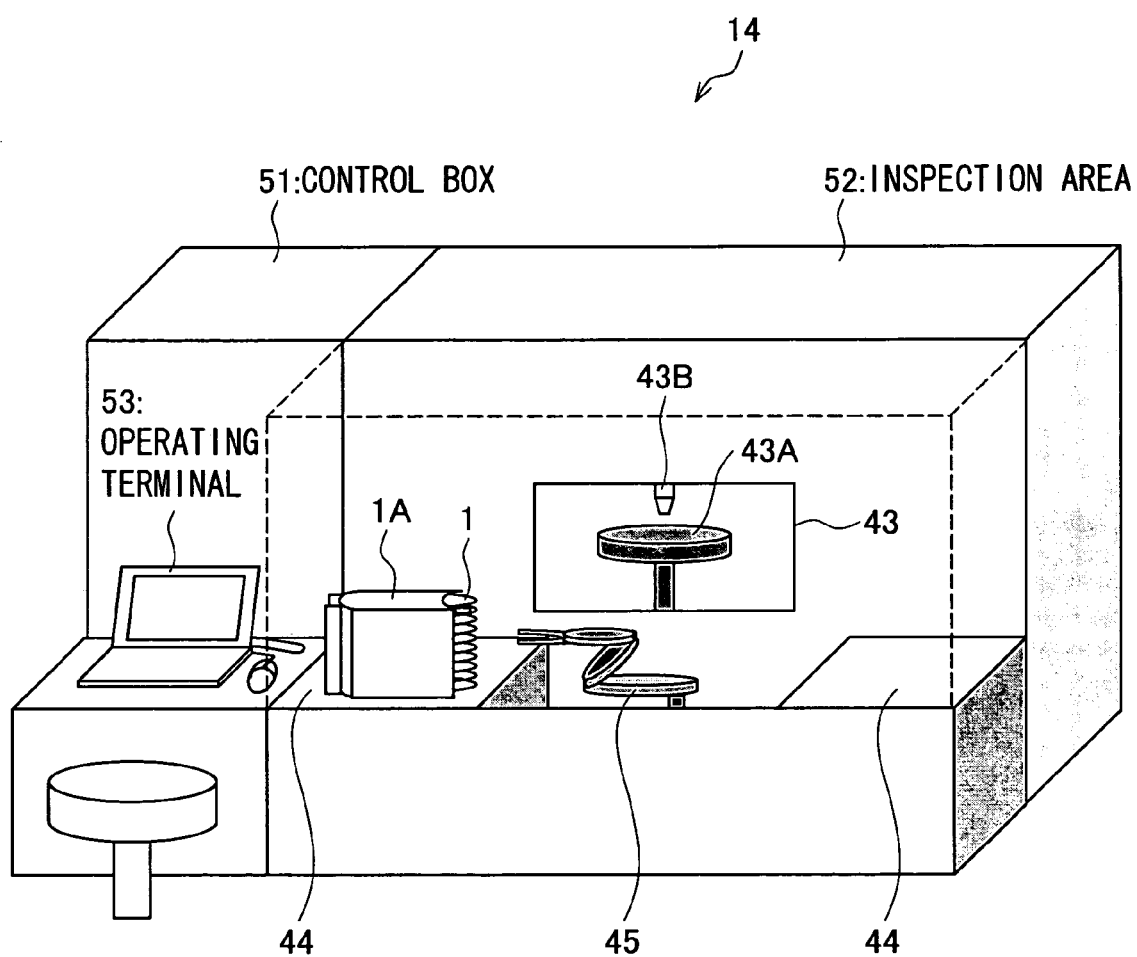
FIG. 3 illustrates an example where the inspection device is an appearance inspection device.

The following describes a specific example of the inspection device 14. FIG. 3 shows a case where the inspection device 14 is an appearance inspection device. As shown in the figure, the inspection device 14 includes a control box 51 and an inspection area 52. The control box 51 is provided with an operating terminal 53. The operator controls the inspecting process by operating the operating terminal 53.

In the inspection area 52, the following members are provided: two cassette retaining sections 44 which are cassette stages, a transportation section 45 which is a transportation arm, and an inspection section 43 which is an inspection area. In the present example, the cassette retaining sections 44 are provided on the incoming side and the outgoing side, respectively. The wafer 1 as a treatment object is stored in a cassette 1A, and this cassette 1A is placed on the cassette retaining section 44 on the incoming side, at first.

The inspection section 43 is provided with an inspection stage 43A and an inspection light source 43B. The transportation section 45 places the wafer 1 on the inspection stage 43A. The inspection light source 43B applies light so that an image on the wafer 1 is obtained. In accordance with the obtained image information, the inspection of a defect is carried out.

The appearance inspection device performs the appearance inspection by, for example, (i) appearance and shape observation using inclined light dark field, inclined laser light, vertically falling light, SEM, or AFM, (ii) the inspection of foreign matters and defects by comparing images, using inclined light dark field, inclined laser light, vertically falling light, SEM, or AFM, (iii) analysis using secondary electrons and X-ray, or the like.

Figure 4:
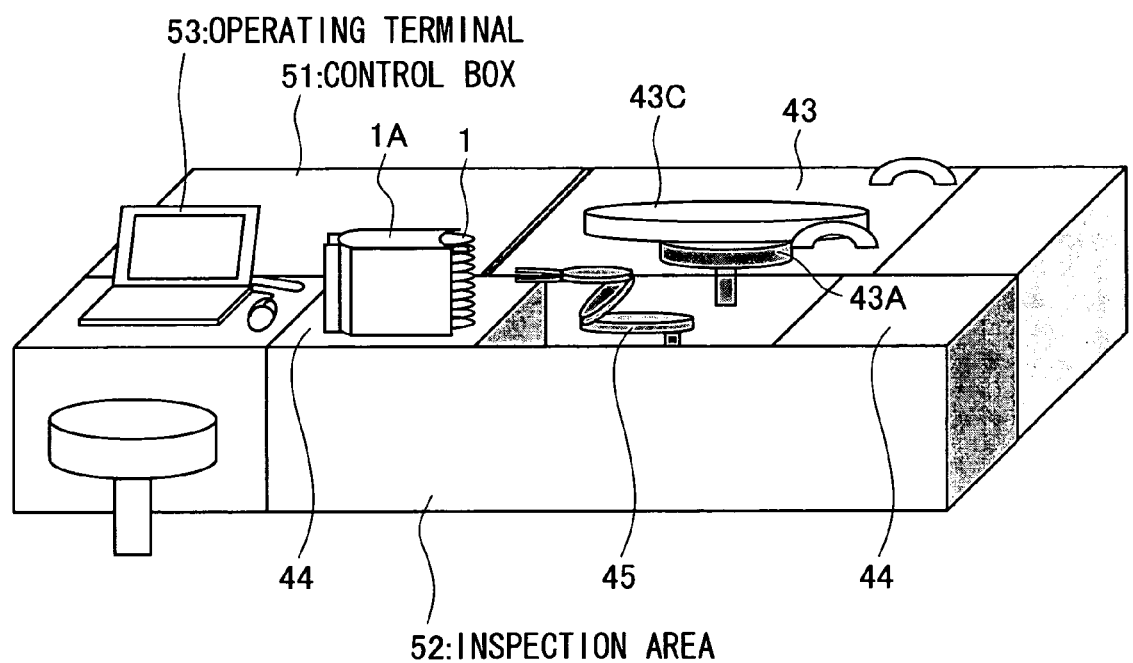
FIG. 4 illustrates an example where the inspection device is an electric property evaluation device.

FIG. 4 shows an example where the inspection device 14 is an electric property evaluation device. As shown in the figure, the inspection device 14 is provided with a control box 51 and an inspection area 52. The control box 51 includes an operating terminal 53. The operator controls the inspecting process by operating the operating terminal 53.

In the inspection area 52, the following members are provided: two cassette retaining sections 44 which are cassette stages, a transportation section 45 which is a transportation arm, and an inspection section 43 which is an inspection area. In the present example, the cassette retaining sections 44 are provided on the incoming side and the outgoing side, respectively. The wafer 1 as a treatment object is stored in a cassette 1A, and the cassette 1A is placed on the cassette retaining section 44 on the incoming side, at first.

The inspection section 43 is provided with an inspection stage 43A and a probe guard setting section 43C. The transportation section 45 places the wafer 1 on the inspection stage 43A. The probe guard setting section 43C sets a probe guard on the wafer 1 so that the electric property of the wafer 1 is evaluated. Based on the electric property evaluation information, the inspection of a defect is carried out.

(Steps of Manufacturing Inspection/Analysis Process)

Figure 5:
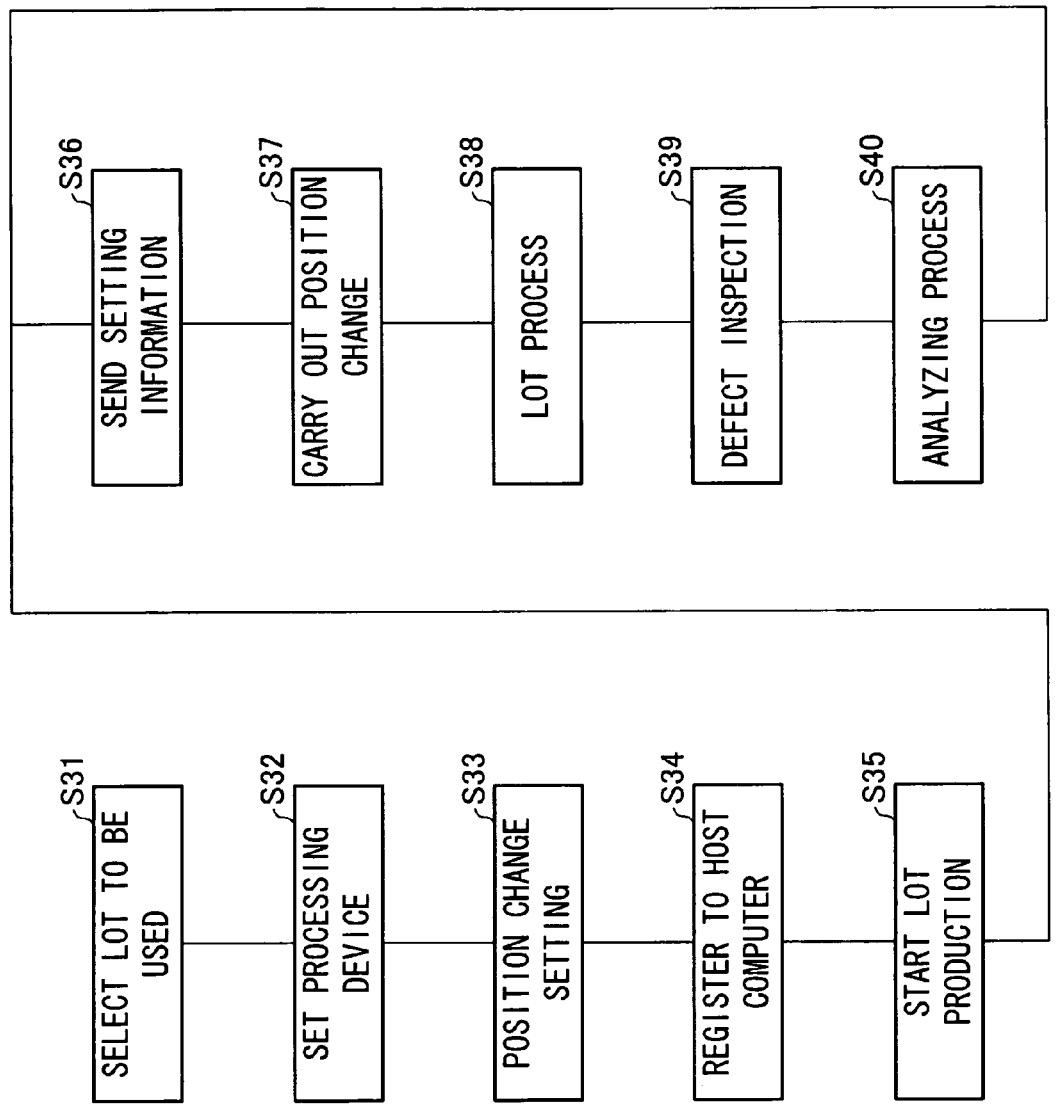
FIG. 5 is a flowchart illustrating the steps performed in a manufacturing inspection and analysis process.

The following will describe the steps of the manufacturing inspection/analysis process in the manufacturing inspection/analysis system, in reference to the flowchart shown in FIG. 5.

First, in which lot of the manufacturing inspection/analysis system the process is carried out is determined (Step 31; hereinafter, steps will be simply referred to as, for example, S31). To the analyzing device 12, information regarding the processing devices 13, which is required for processing the selected lot is inputted by the operating using the input section 26 (S32). This information is forwarded to the position change setting section 25. In reference to the types of the processing devices 13 to be used and the order of the steps, the position change setting section 25 determines in what manner the position change of the treatment object is set in each processing device 13 (S33). Also, the information of the processing devices 13 to be used is supplied from the analyzing device 12 to the host computer 11, and is registered in the host computer 11 (S34). Thereafter, the host computer 11 instructs the analyzing device 12, processing devices 13, transportation devices 15, and inspection device 14 to start the lot production.

After the start of the lot production, first, the setting information regarding the position change in each processing device 13, which has been set by the position change setting section 25, is supplied to each processing device 13 by the communication section 21 (S36). In each processing device 13, the communication section 31 receives the setting information and the information is transferred to the position change section 32. Based on the received setting information, the position change section 32 performs the position change of the treatment object (S37). Then the processing section 35 subjects the treatment object to the process supposed to be performed by the processing device 13, so that the lot process is carried out (S38).

After the treatment object is subjected in sequence to the necessary processes of the respective processing devices 13, the inspection device 14 performs the inspection of a defect (S39). The defect information generated by the inspection device 14 is stored in a defect memory section 42, and is supplied to the analyzing device 12 via the communication section 41. Based on the positional information supplied from each processing device 13 and the defect information supplied from the inspection device 14 via the communication section 41, the analyzing device 12 performs analysis in order to specify in which processing device 13 the defect occurred (S40). Thereafter, the steps S36 to S40 are repeated until it is instructed to stop the lot production.

In an ideal situation, the repeat of the steps from S36 to S40 is always carried out while the manufacture is conducted. This makes it possible to detect the occurrence of an abrupt fault (defect), thereby reducing the damage. In reality, the repeat may be carried out in each manufacturing inspection/analysis system, once in a day. In the product development stage, the repeat may be performed for all of the processing steps of a production prototype. This makes it possible to speed up the development time.

Carrying out the repeat at the time of conducting repair or periodical maintenance of the processing devices 13 is beneficial for the reason that a defect which cannot be detected in the monitoring after the start-up may become explicit and detected in a few steps later.

(Example of Processes)

Figure 6:
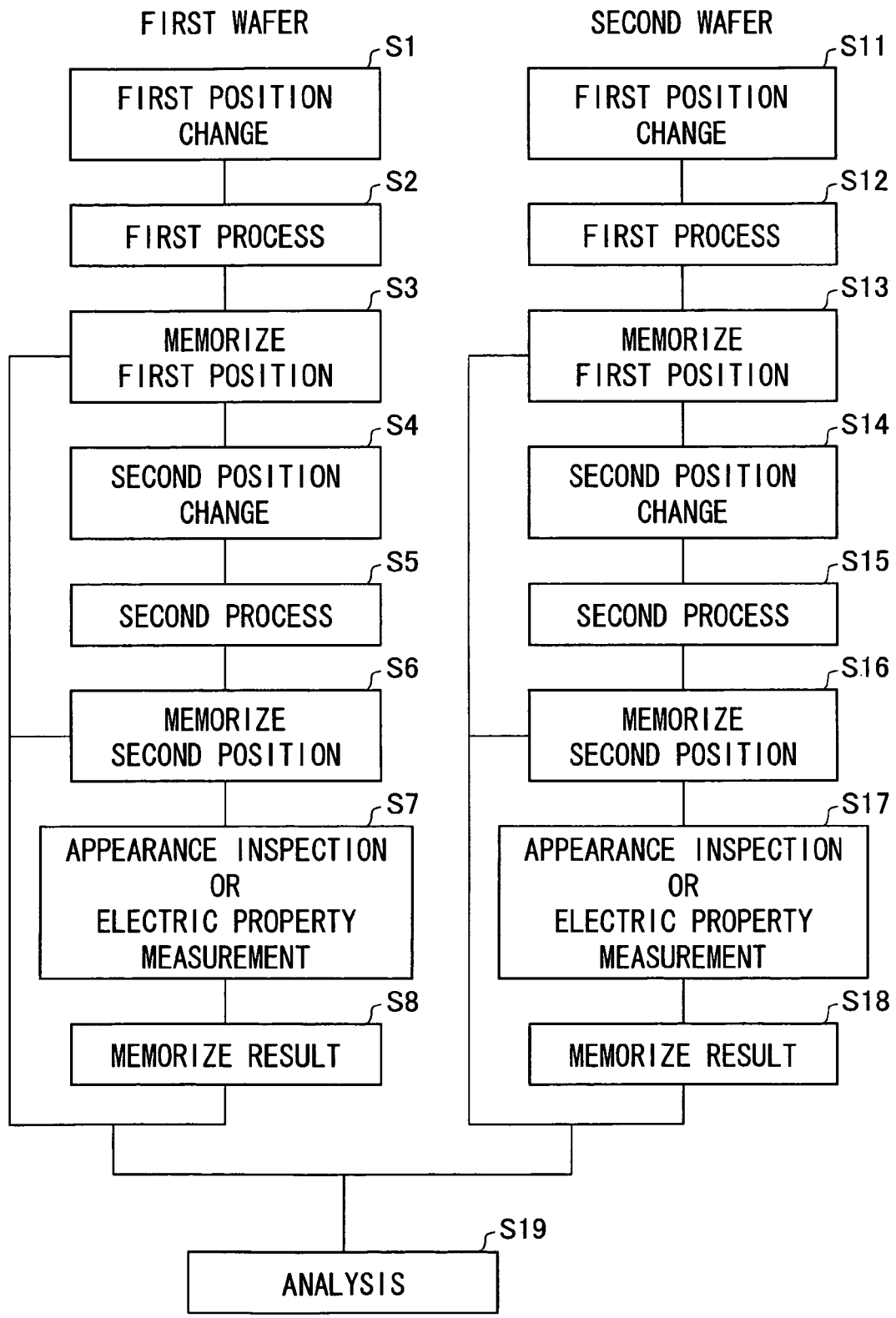
FIG. 6 is a flowchart showing an example of a process performed by the manufacturing inspection/analysis system.

FIG. 6 shows a flowchart regarding an example of the processes in the manufacturing inspection/analysis system. In this example, a plurality of wafers each having a notch are serially transported to the manufacturing inspection/analysis system in units of cassettes, so as to be subjected to the processes. It is noted that the wafer, which is the treatment object in the present example, is made up of a plate-shaped member, e.g. a glass plate or a resin plate.

FIG. 6 shows the flow of processes in regard of two wafers (first wafer and second wafer). Also, two processes (first process and second process) are carried out by two processing devices 13 (first and second processing devices), respectively. Based on the inspection results in the respective processes, the analysis of defect is performed. Alternatively, the analysis may be carried out based on at least three processes performed on at least three wafers.

(First and Second Processes)

Figure 7:
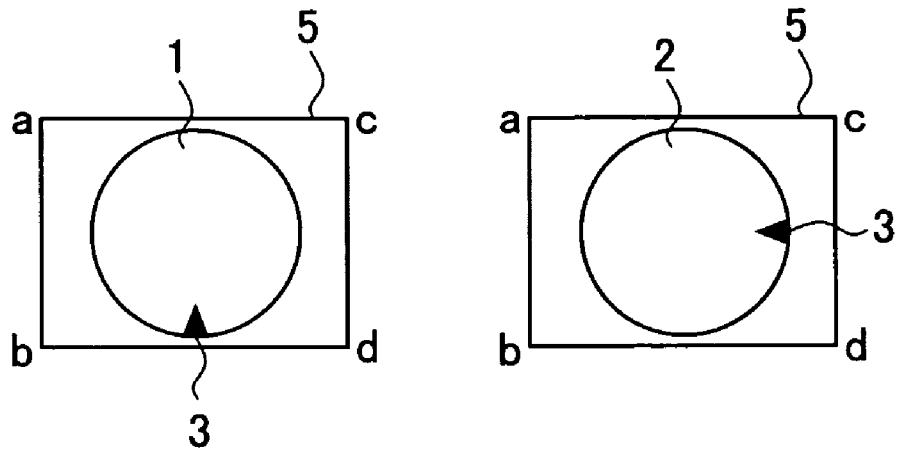
FIG. 7(a) illustrates in what matter first and second wafers are placed at the time of performing a first process, in the example shown in FIG. 6.
FIG. 7(b) illustrates in what matter first and second wafers are placed at the time of performing a second process.
FIG. 7(c) illustrates an example of a defect inspection result.
Figure 7:
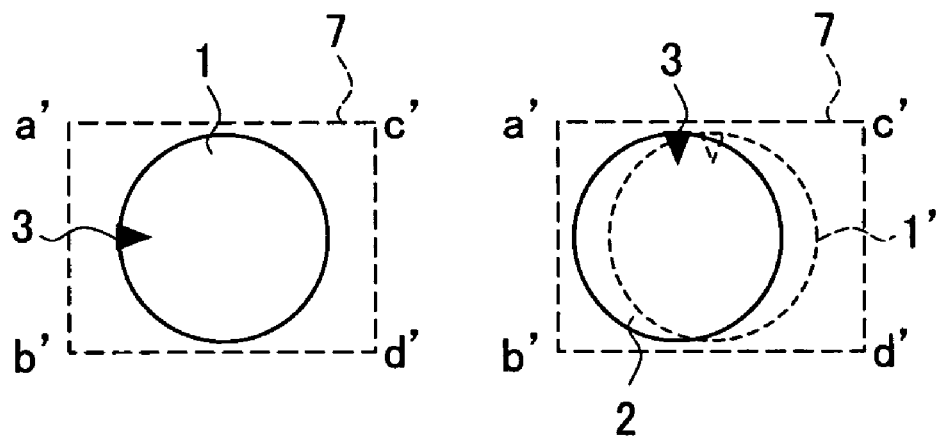
Figure 7:
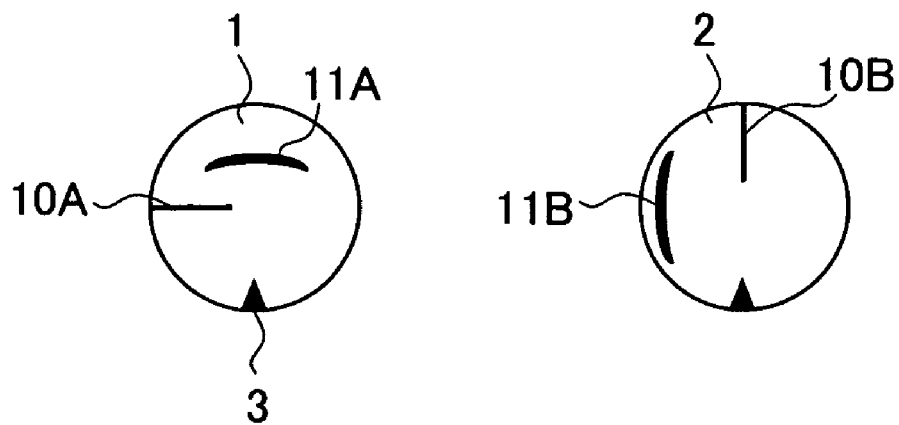

As shown in the left side of FIG. 7(a), first, a first wafer 1 is placed in a polishing chamber 5 of a CMP device which is the first processing device 13 that performs the first process (e.g. CMP (Chemical-Mechanical Polish)). Before the placement, in the cassette in which the first wafer 1 is stored, a first position change section 32 changes the orientation of the first wafer 1 by rotating the wafer horizontally (S1). Then the first wafer 1 whose orientation has been changed in the cassette is transported to and placed in the polishing chamber 5, by means of the first transportation section 36. On this occasion, as shown in the left side of FIG. 7(a), the first wafer 1 is placed in such a manner that the notch 3 of the first wafer 1 comes closest to the side b-d of the polishing chamber 5.

In S2, the first wafer 1 is subjected to the first process by the CMP device. After the completion of the first process, the first transportation section 36 returns the first wafer to the inside of the cassette. Also, a first position memory section 34 memorizes, as a first position, the orientation of the first wafer 1, which has been changed in S1 by the first position change section 32 (S3). As a result, the first position memory section 34 memorizes the position of the first wafer 1 when the first process is carried out thereto, i.e. memorizes in which orientation the first wafer 1 takes in the polishing chamber 5.

Subsequently, in the cassette storing the second wafer 2, the first position change section 34 changes the orientation of the second wafer 2, by rotating the second wafer 2 horizontally (S11). Then the second wafer 2 whose orientation has been changed in the cassette is transported to and placed in the polishing chamber 5, by the first transportation section 36. On this occasion, as shown in the right side of FIG. 7(a), the second wafer 2 is placed so that the notch 3 of the second wafer 2 comes closest to the side c-d of the polishing chamber 5.

In S12, the CMP device subjects the second wafer 2 to the first process. When the first process is completed, the first transportation section 36 returns the second wafer 2 to the inside of the cassette. Also, the first position memory section 34 memorizes, as a first position, the orientation of the second wafer 2, which has been changed by the first position change section 32 in S11 (S13). As a result, the first position memory section 32 memorizes the position of the second wafer 2 when the wafer 2 is subjected to the first process, i.e. memorizes in which orientation the second wafer 2 takes in the polishing chamber 5.

Thereafter, as shown in the left side of FIG. 7(b), the first wafer 1 is placed in an etching chamber 7 of a dry etching device which is a second processing device 13 that subjects the first wafer 1 to a second process (e.g. dry etching). Before the placement, in the cassette storing the first wafer 1, the second position change section 32 changes the orientation of the first wafer 1 by rotating the first wafer 1 horizontally (S4). Then the first wafer 1, whose orientation has been changed in the cassette, is transported to and placed in the etching chamber 7 by the second transportation section 36. On this occasion, as shown in the left side of FIG. 7(b), the first wafer 1 is placed so that the notch 3 of the first wafer 1 comes closest to the side a'-b' of the etching chamber 7.

In S5, the dry etching device subjects the first wafer 1 to the second process. After the completion of the second process, the second transportation section 36 returns the first wafer 1 to the inside of the cassette. The second position memory 34 memorizes, as a second position, the orientation of the first wafer 1, which has been changed by the second position change section 32 in S4 (S6). As a result, the second position memory section 34 memorizes the position of the first wafer 1 when the first wafer 1 is subjected to the second process, i.e. memorizes in which orientation the first wafer 1 takes in the etching chamber 7.

Subsequently, in the cassette that stores the second wafer 2, the second position change section 32 changes the orientation of the second wafer 2, by rotating the second wafer 2 horizontally (S14). Then the second wafer 2, whose orientation has been changed in the cassette, is transported to and placed in the etching chamber 7, by the second transportation section 36. On this occasion, as shown in the right side of the FIG. 7(b), the second wafer 2 is placed so that (i) the notch 3 of the second wafer 2 comes closest to the side a'-c' of the etching chamber 7, and (ii) the second wafer 2 is placed at a location which is horizontally distanced from the normally-placed location, in a predetermined orientation and for a predetermined length. In the right side of FIG. 7(b), a dotted line 1' indicates the normally-placed location before the horizontal movement.

In S15, the dry etching device subjects the second wafer 2 to the second process. After the completion of the second process, the second transportation section 36 returns the second wafer 2 to the inside of the cassette. The second position memory section 34 memorizes, as a second position, (i) the orientation of the second wafer 2, which has been changed by the second position change section 32 in S14 and (ii) a length of the horizontal movement of the second wafer 2 by the second transportation section (S16). Therefore, the second position memory section 34 memorizes a position of the second wafer 2 when the second wafer 2 is subjected to the second process, i.e. memorizes in which orientation the second wafer 2 takes and at what location the second wafer 2 is placed, in the etching chamber 7.

Thereafter, in S7 and S17, the inspection device 14 subjects the first and second wafers 1 and 2 to the defect inspections (e.g. detection of a foreign matter or a defect by image comparison using vertically falling light). FIG. 7(c) shows an example of the results of the defect inspections. It is noted that the left side of FIG. 7(c) shows the result of the defect inspection of the first wafer 1, while the right side of FIG. 7(c) shows the result of the defect inspection of the second wafer 2.

In S8 and S18, the defect memory section 42 memorizes the characteristics of the defects, which are shown in the results of the defect inspections performed in S7 and S17. Non-restrictive examples of the characteristics are, coordinates on the basis of a reference point (e.g. notch) on the wafer, distribution, shape, size, composition, number, and density. In the example shown in FIG. 7(c), scratches 10A and 10B and foreign matters 11A and 11B are detected. These matters are memorized in the defect memory section 42, as the aforesaid characteristics.

(Analyzing Process)

Subsequently, in S19, the analyzing process section 23 performs the analysis based on the information stored in the first position memory section 34, second position memory 34, and defect memory section 42. More specifically, in regard of the first wafer 1, a relative positional relationship between the following (i) and (ii) is analyzed: (i) the characteristics (e.g. distributions of scratch 10A and foreign matter 11A) stored in the defect memory section 42, as information concerning where defects occur, and (ii) the positions memorized by the first and second position memory sections 34, in connection with the first and second processes.

Figure 8:
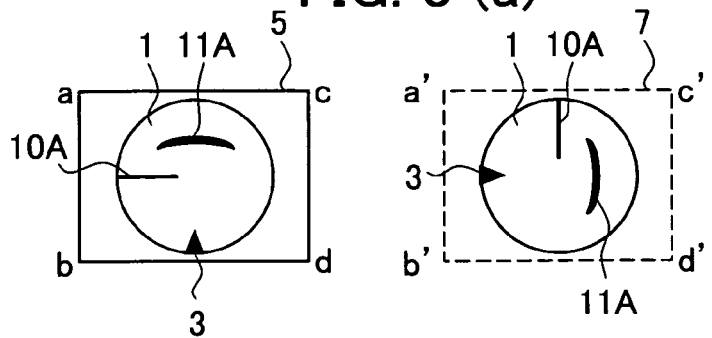
FIG. 8(a) illustrates the relationship between the characteristic of a defect in the first wafer and the locations of the first wafer in the first and second process, respectively.
FIG. 8(b) illustrates the relationship between the characteristic of a defect in the second wafer and the locations of the second wafer in the first and second process, respectively.
FIG. 8(c) illustrates the relationship between the characteristic of a defect in the first wafer and the locations of the second wafer in the first process.
FIG. 8(d) illustrates the relationship, in the second process, between the location of the first wafer and the location of the second wafer.
Figure 8:
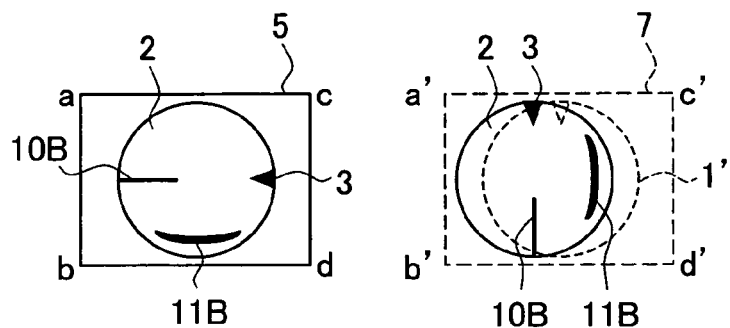
Figure 8:
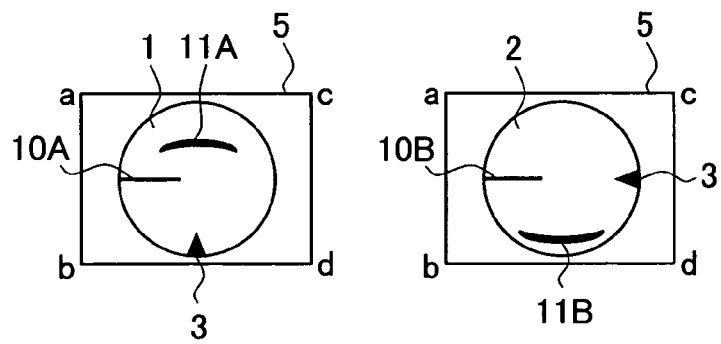
Figure 8:
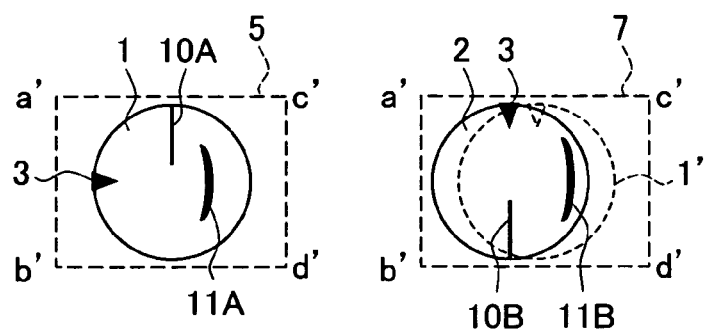

The relationship between the characteristics of the defects on the first wafer 1 and the position of the first wafer 1 in the first process is shown in the left side of FIG. 8(a). The relationship between the characteristics of the defects on the first wafer 1 and the position of the first wafer 1 in the second process is shown in the right side of FIG. 8(a). These results are stored in the relative position memory section 22.

In a similar manner, the relationship between the characteristics of the defects on the second wafer 2 and the position of the second wafer 2 in the second process is shown in the right side of FIG. 8(b). These results are stored in the relative position memory section 22.

Subsequently, based on this information of the relative position stored in the relative position memory section 22, the position of the first wafer 1 and the position of the second wafer 2 in the first process are recognized. FIG. 8(c) shows the recognized positions.

According to the figure, the scratch 10A on the first wafer 1 extends from the wafer edge on the side a-b toward the center of the wafer (the notch is on the side b-d). The scratch 10B on the second wafer 2 also extends from the wafer edge on the side a-b towards the center of the wafer (the notch is on the side c-d).

In the meanwhile, the distribution of the foreign matters 11A on the first wafer 1 is arc-shaped and the foreign matters 11A locate between the center of the wafer and the side a-c. On the other hand, the distribution of the foreign matters 11B on the second wafer 2 are also arc-shaped but the foreign matters 11B locate in the vicinity of the edge on the b-d side (i.e. far from the center of the wafer).

According to these results, in the first process, only the scratches 10A and 10B have an identical relative position with respect to the processing device 13, among the defects on the first and second wafers 1 and 2. As a result, it is possible to conclude that the scratches 10A and 10B occurred in the first process.

Subsequently, the respective positions of the first and second wafers 1 and 2 in the second process are recognized. FIG. 8(d) shows the recognized positions.

In the figure, the scratch 10A on the first wafer 1 extends from the wafer edge on the side a'-c' toward the center of the wafer (the notch is on the side a'-b'). Meanwhile, the scratch 10B on the second wafer 2 extends from the wafer edge on the side b'-d' towards the center of the wafer (the notch is on the side a'-c').

On the other hand, the positions of the foreign matter 11A on the first wafer 1 and the foreign matter 11B on the second wafer 2 are identical with each other with respect to the etching chamber 7. For this reason, it is possible to conclude that the foreign matters 11A and 11B be both adhered in the second processing device.

As a result of the above-described analysis by the analyzing process section 23, it is possible to recognize in which process a defect on the wafer occurred. Based on the result of the analysis, an improvement is conducted to the processing device 13 corresponding to the process where the defect occurred according to the analysis.

In the example above, the analysis is based on the relationship between a defect in each processing device 13 and the position of the wafer. Alternatively, the analysis may be based on each defect. For example, the analysis is carried out in the following manner, if scratches 10A and 10B are analyzed.

Provided that the scratches 10A and 10B are assumed to be caused by a single cause, first, the scratch 10A on the first wafer 1 is superposed onto the scratch 10B on the second wafer 2. Assuming that a line extending from the scratch to the center of the wafer indicates a reference 0°, the angle of a notch 3 on the first wafer 1 is about 270° in the clockwise orientation. Meanwhile, the angle of a notch 3 on the second wafer 2 is about 180° in the clockwise orientation. The relationship between the notch 3 on the first wafer 1 and the notch 3 on the second wafer 2 corresponds to the first process. The relationship between the notches 3 does not correspond to the second process. Furthermore, by superposing the notches, it is possible to specify the processing device where defects occur, based on the angles of the defects.

In the analysis above, it is difficult to specify in which processing device 13 a defect occurs, if the combination of the positions of the wafers 1 in the first process is identical with combination of the positions of the wafers 1 in the second process. Therefore, all of the processing devices 13 in a series of manufacturing processes preferably have different combinations of the positions of the wafer 1.

Alternatively, three or more wafers may be used, and the degrees of the rotational angle and horizontal movement may be minutely set (e.g. the rotational angle changed by one degree or ten degrees, or the horizontal movement by one millimeter or ten millimeter). In such cases, although the number of the combinations of the positions is increased, the difference between the positions of defects with respect to the reference position is small, and hence it is difficult to specify in which processing device 13 a defect occurs.

For example, in a case where the aforesaid analysis is carried out in a mid-size factory where more or less 1000 manufacturing devices are provided, 1000 types of characteristics having different positions are required. A defect on account of the processing device 13 does not accurately occurs at the same position, i.e. defects slightly deviate from one another. That is, defects occur at relatively similar locations, from a macroscopic viewpoint. On this account, in a case where the positions of the processing devices 13 are only slightly deviate from one another, the analysis cannot be properly carried out on account of the deviation between defects. On this account, an amount of change between the positions in the position change must be large to some extent. Taking into account the above, the number of the combinations of the positions can be increased by increasing the number of wafers 1 which are considered as one unit.

Realistically, more than 1000 combinations can be achieved as follows: 25 wafers 1 are regarded as one unit, and three of these wafers 1 are rotated in-plane so that the angles of the notches 3 are 30°, 120°, and 255° with respect to the reference 0°, while the angles of the notches of the remaining wafers 1 are set at 0°.

More specifically, first, wafers 1 are inserted into slots 1-25 of the cassette, respectively. The angles of the notches 3 at this stage are all identical to each other. In reference to this orientation (assumed as 0°) of the notches 3, in the first process, the angle of the notch 3 of the wafer 1 in the slot 1 is changed for $\alpha°$, the angle of the notch 3 of the wafer 1 in the slot 2 is changed for $\beta°$, and the angle of the notch 3 of the wafer 1 in the slot 3 is changed for $\theta°$. The first process is carried out while the angles of the notches 3 of the remaining wafers 1 in the slots 4-25 are all set at 0°. Subsequently, in the second process, the angle of the notch 3 of the wafer 1 in the slot 1 is set at $\beta°$, the angle of the notch 3 of the wafer 1 in the slot 2 is set at 0°, the angle of the notch 3 of the wafer 1 in the slot 3 is set at $\alpha°$, and the angle of the notch 3 of the wafer 1 in the slot 4 is set at $\theta°$. The second process is carried out while the notches 3 of the wafers 1 in the remaining slots 5-25 are set at 0°. In this manner, in a case where 25 wafers 1 are distinguishable on account of, for example, slots, the order of the angles is as follows: one wafer 1 with $\alpha°$, one wafer 1 with $\beta°$, one wafer with $\theta°$, and 22 wafers with 0°. Therefore the number of combinations of the positions is $_{25}P_1 \times _{24}P_1 \times _{23}P_1 \times _{22}C_{22} = 25 \times 24 \times 23 \times 1 = 13800$. This number of the combinations is large enough for large-scale manufacturing systems.

Now, the angle of the notch 3 is discussed. In (a1) and (a2) in FIG. 26, the angles of the notches 3 are 0° and 180° in the first and second processes, respectively. In (a3) in the figure, the defect inspection by the inspection device 14 is illustrated. In (a4) in the figure, how the cause of a defect is analyzed is shown. As the figure shows, in a case where the combination of the angles of the notches 3 is 0° and 180°, it is occasionally indeterminable whether a defect occurred in the first process or in the second process.

Figure 26:
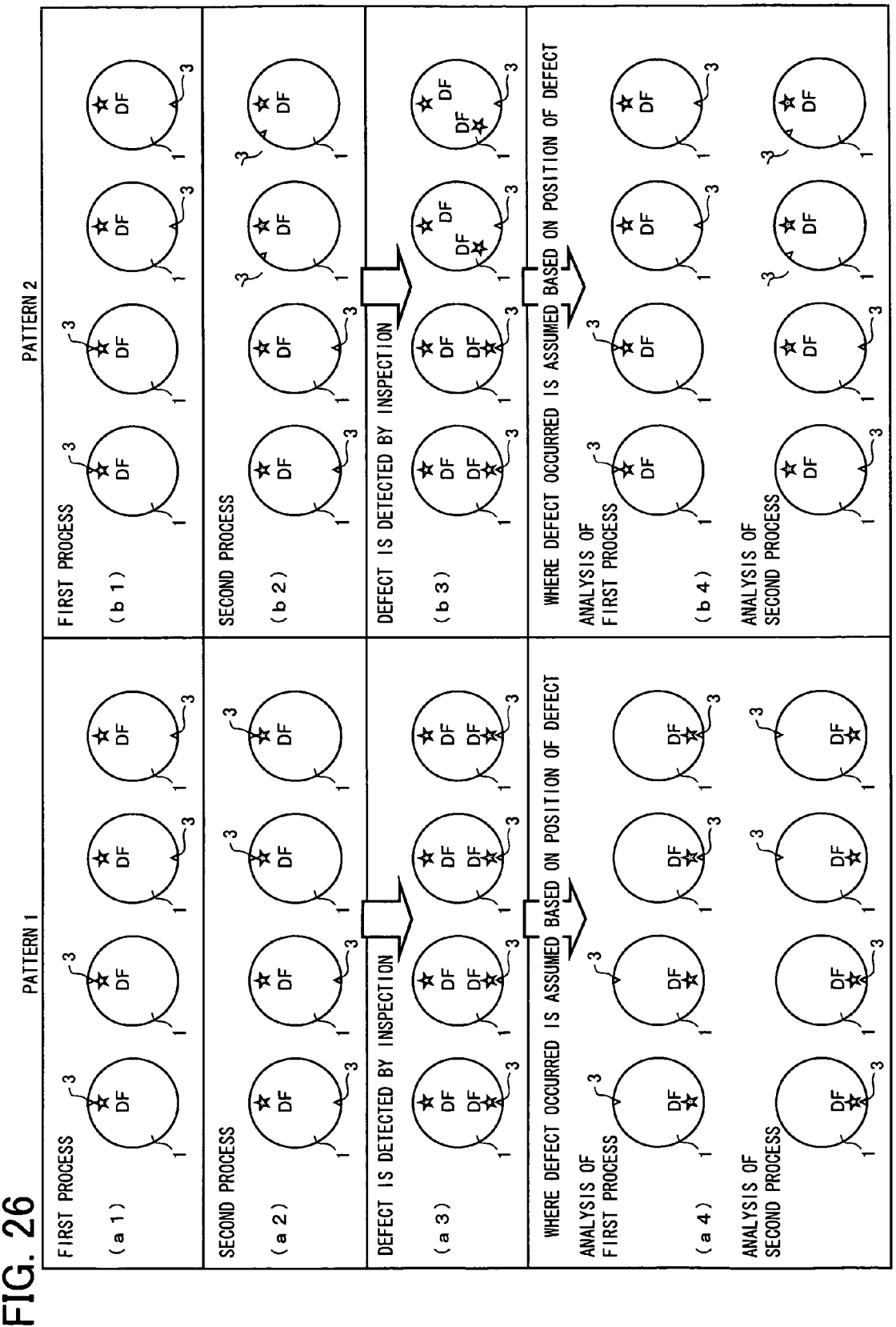
FIG. 26 shows an example where the analysis of a defect is properly carried out with a combination of angles of the notch and an example where the analysis of a defect is not properly carried out with another combination of angles of the notch.
Figure 27:
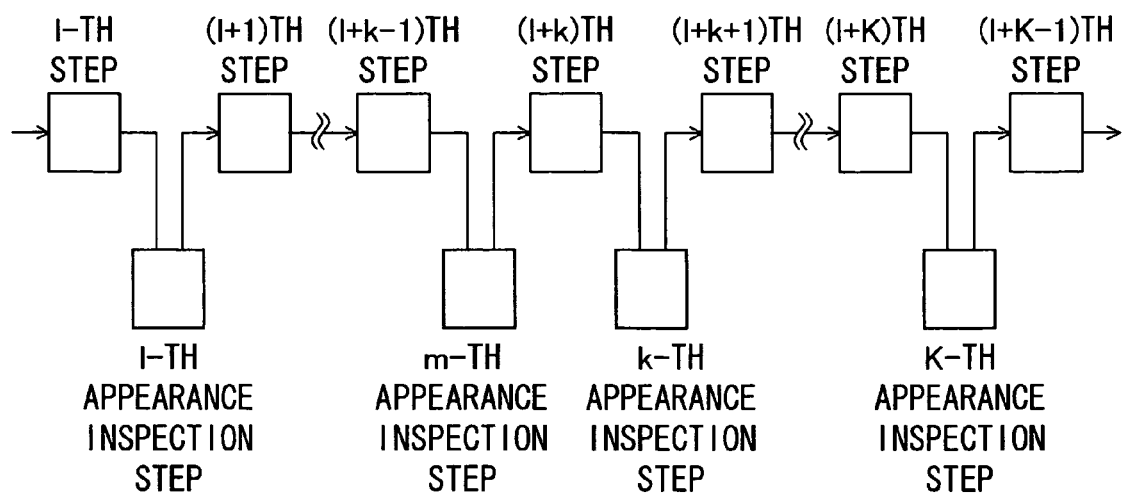
FIG. 27 shows a conventional method of detecting and monitoring foreign matters and defects.
Figure 28:
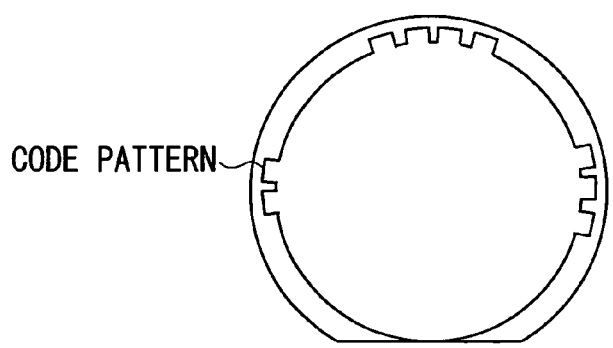
FIG. 28 shows an example where an ID of a manufacturing device having been treated is patterned, as a code pattern, on a wafer, in order to specify which manufacturing device generates a shape defect.
Figure 29:
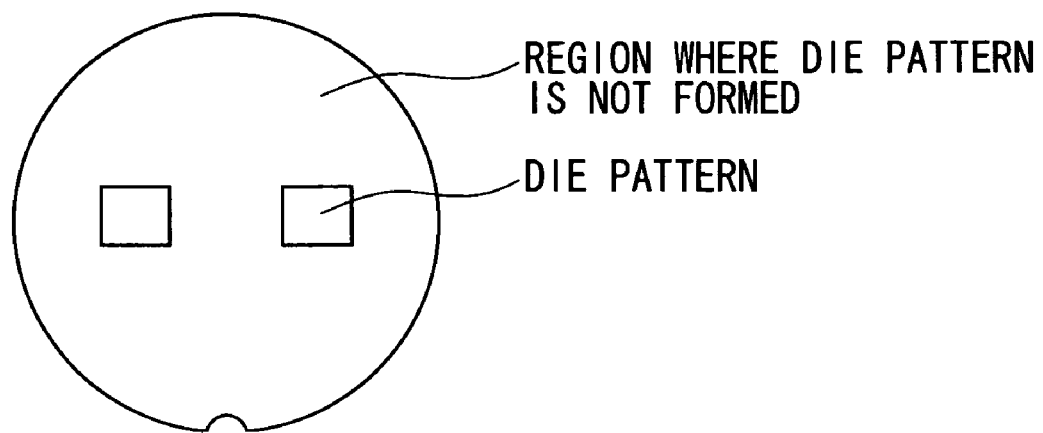
FIG. 29 shows a conventional example of forming a die pattern on a part of a monitor wafer in order to highly precisely monitor where a foreign matter or defect locates.

In the meanwhile, (b1) in FIG. 26 shows a case where the angles of the notches 3 are 0° and 180° in the first process while the angles of the notches 3 are 0° and 135° in the second process. In (b3) in the figure, how the defect inspection is carried out by the inspection device 14 is shown. In (b4) in the figure, how a cause of the defect is analyzed is illustrated. In this manner, changing the angles of the notches 3 as above makes it possible to properly determine whether the defect occurred in the first process or in the second process.

That is, the set angles of the notches 3 must meet the following requirements: (1) the angles are not symmetrical with respect to the center of a treatment object; (2) the difference between angles of a pair of the notches 3 differs from one pair to another; and (3) at least one of the conditions (1) and (2) is met.

In the example above, the treatment object, which is the target of defect inspection, is a semiconductor wafer having a notch. Alternatively, the treatment object may be a semiconductor wafer that has an orientation flat face or other reference points (e.g. a mark for alignment, a circuit pattern of the product, or the like may be used as a reference point). Also, in addition to silicon, silicon compound, and nitride semiconductor, the treatment object may be a glass plate used for liquid crystal screens and displays, or a resin plate used for solar cells, displays, and illuminations. The shape and material of the object to be subjected to the defect inspection can be optionally determined, as long as the treatment object is a flat plate. Since the shape of the treatment object is not necessarily flat, the object may be a three-dimensional figure such as a sphere. As to the change of the relative positions, the process may be carried out after the changes of the positions of all wafers in the cassette are completed. The treatment objects are not necessarily transported in units of cassettes. Therefore, each treatment object may be individually transported. In such a case, a wafer subjected to a process performed in one processing device 13 may be regarded as a first wafer 1, while a wafer subjected to the next process may be regarded as a second wafer 2. The step of memorizing the positions of the wafer 1 in each process may be carried out before performing each process. In the example above, CMP and dry etching are carried out as the processes. The processes, however, may be other manufacturing processes.

(Details of Horizontal Movement)

In the above-described embodiment, the second process to which the second wafer 2 is subjected includes the horizontal movement of the wafer 1, in addition to the rotation of the wafer 1 in order to change the orientation of the notch 3. The objective of the above is to support a case where a defect is shaped like a concentric circle around the center of the wafer.

Figure 25:
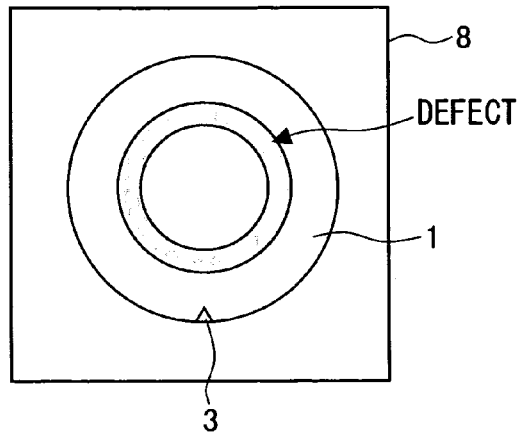
FIG. 25(a) shows a state where a concentric defect occurs in a wafer mounted in the normal position with respect to a chamber.
FIG. 25(b) shows a state where a concentric defect occurs in a wafer mounted in a position at right angles to the normal position, with respect to the chamber.
FIG. 25(c) shows a state where a concentric defect occurs in a wafer mounted in a position which is horizontally away from the normal position.
Figure 25:
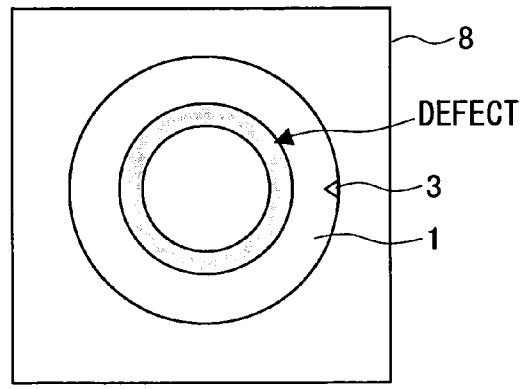
Figure 25:
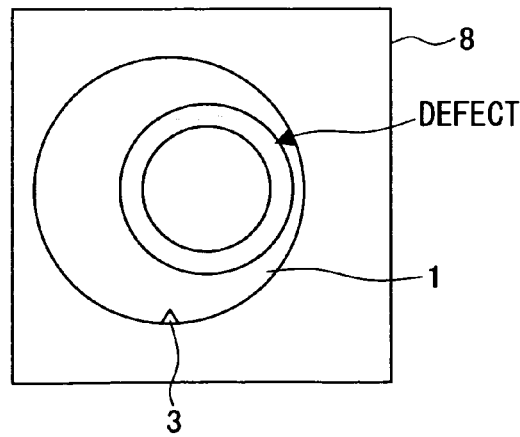

FIG. 25(a) shows a case where a concentric defect occurs on a wafer 1 which is in a normal position with respect to the chamber 8 that functions as a processing section 35. FIG. 25(b) shows a case where a concentric defect occurs on a wafer 1 which is at a location horizontally away from the normal position, with respect to the chamber 8. Inspecting the wafers 1 in the respective cases and analyzing defects, it is found that the locations of the defects with respect to the respective notches 3 are identical with each other. It is therefore impossible to specify which processing device 13 caused the defects.

In the meanwhile, FIG. 25(c) shows a case where a concentric defect occurs on a wafer 1 which is horizontally distanced from the normal position, with respect to the chamber 8. In this case, the location of the defect with respect to the notch 3 is different as compared to the wafer 1 at the normal position. On this account, it is possible to specify which processing device 13 caused the defect. In summary, the position change process preferably includes the horizontal movement, in a case where it is uncertain whether a defect is concentric or not.

In the case where a defect or foreign matter occurs/exists in a concentric manner with respect to the center of the wafer 1, the relative position change may be carried out by turning over the wafer.

The following discusses in what manner a concentric defect occurs. For example, in a case where a film is formed by a hot wall batch device, the periphery of the wafer 1 is close to a heater while the center of the wafer 1 is far from the heater. Because of this difference in distance, in some cases, the periphery of the wafer has a high temperature while the center of the wafer has a low temperature. In general, a film is rapidly formed in a hot environment, while the formation of a film is slow in a cold environment. On this account, the wafer 1 is thick at the periphery but thin at the center. Taking a gate insulating film about 3-10 nm thick as an example, a thin film is likely to be suffered from dielectric breakdown. The center of the film may not be sufficiently thick.

If the wafer 1 is, with respect to the device, horizontally displaced from the normal position, the distance from the heater is different and hence the thickness of the film is also different. (Incidentally, if the thickness of the film is the factor of determination, the analysis is carried out here.) If the measurement of electric properties proves that the circle of the defect is displaced, it is possible to assume which device causes the defect, by inspecting the locations.

Assume that a sheet-feed film formation device supplies raw gas through a shower head above the wafer, and a part of the shower head produces dust on account of maintenance failure. If the film formation is carried out while the wafer 1 (or the processing stage) is rotated in order to improve the evenness of the film, the locations of dust are equidistant from the center of the rotation. Moving the location of the wafer 1 causes the center of the circle of the dust to be deviated from the center of the wafer 1. Taking notice of this deviation, it is possible to assume which processing device 13 caused the defect.

(Method of Identifying Wafer)

To analyze the defect, it is necessary to precisely associate (i) positional information stored in the position memory section 34 of each processing device 13 and (ii) defect information memorized in the defect memory section of the inspection device 14 with (iii) each of the wafers 1 having been subjected to the process. The wafer 1 is stored in the cassette when the wafer 1 is transported between the processing devices 13. On this account, it is possible to specify the wafer 1 by referring to the cassette number (lot number) and the slot number (which have been recorded) of the cassette. The positional information is, for instance, arranged such that, in a particular process, a wafer 1 in the fifth slot of a cassette 151 is rotated for 30°, while wafers 1 in first to fourth and sixth to 25th slots are rotated for 0°.

In a case where each wafer 1 is individually transported without using cassettes, it is necessary to identify each wafer 1. The identification of wafers may be carried out by reading a barcode on each wafer 1. In such a case, for example, the following information is memorized: a wafer 1 with a wafer code 1 is rotated for 30° and the remaining wafers 1 are rotated for 0° in the first processing device 13, while a wafer 1 with a wafer code 50 is rotated for 30° while the remaining wafers 1 are rotated for 0° in the second processing device 13. In this case, when only a defect on the wafer 1 with the wafer code 50 is deviated for 30°, it is possible to assume that the second processing device 13 be a cause of the defect.

In a case where a plurality of processing devices 13 are used and each of these processing devices 13 carries out the analysis, it is necessary to deal with a plurality of wafers 1 as one unit. In this case, it is necessary to cause each of the processing devices 13 to memorize which wafer 1 is subjected to the process, in chronological order. This makes it possible to consider as if a plurality of wafers 1 are stored in one cassette (lot).

Alternatively, the associations between the wafers 1 may be made through visual observation by an operator.

Examples of the information memorized by the position memory section 34 of each processing device 13 and supplied to the analyzing device 12 are: cassette number (ID), slot number (ID), processing device number (ID), the order of wafers 1 to be processed in each processing device 13, and relative positions of each wafer 1 in the respective processes. Examples of the information memorized by the defect memory section 42 of the inspection device 14 and supplied to the analyzing device 12 are: cassette number (ID), slot number (ID), inspection device number (ID), a location of a defect on each wafer 1, the number of defects on each wafer 1, the distribution of defects on each wafer 1, the density of defects on each wafer 1, the shape of a defect on each wafer 1, the size of a defect on each wafer 1, the elements and compositions of a defect on each wafer 1, the color of a defect on each wafer 1, and whether a defect on each wafer 1 is protruding or concave.

Example 1

Of Position Change

Figure 9:
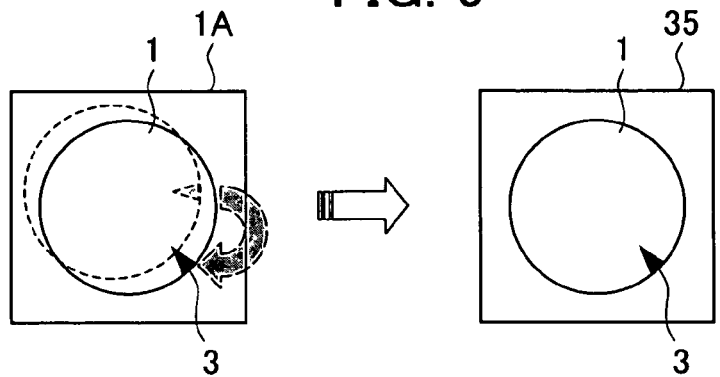
FIG. 9 shows an example 1 of position change.

FIG. 9 shows a case where the position change section 32 changes the position of the notch 3 by horizontally rotating the wafer 1, and then the wafer 1 is placed in the processing section 35. The position of the notch 3 of each wafer 1 is optionally changed by the position change section 32, so that the position of the wafer 1 in the processing section 35 is changed. For example, before the wafer 1 is subjected to the process, the wafer 1 in the cassette 1A is horizontally rotated or linearly moved by drive means of the position change section 32, such as a table, pin, stepping motor, timing belt, and gear. Concurrently, the center of the wafer 1 and the position of the notch 3 are detected by, for example, an optical sensor. Subsequently, the wafer 1 is rotated in-plane or linearly moved by the drive means, so that the position and orientation of the recognized notch 3 is optionally changed. The wafer 1 is then transported to the processing section 35 by the transportation section 36, and the wafer 1 is subjected to the process.

Figure 30:
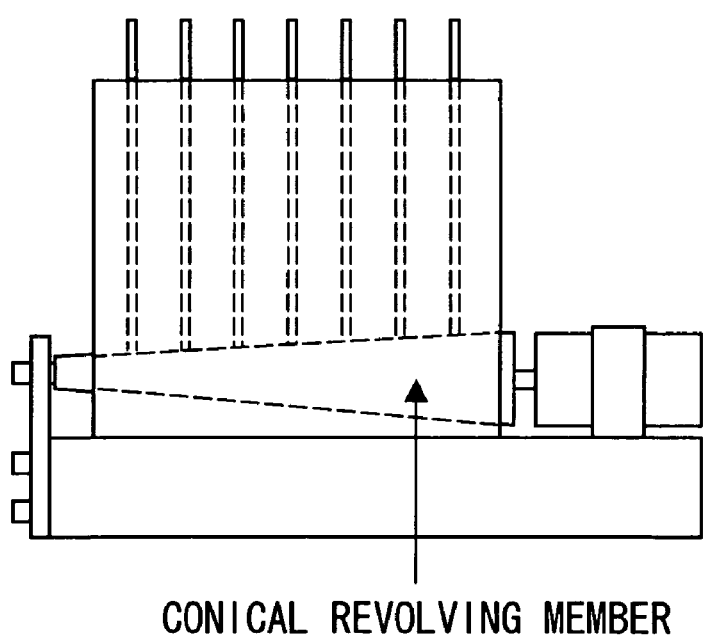
FIG. 30 shows an example to change the position of the orientation flat face of a wafer in a cassette, using a conical revolving member.

The method of changing the orientation of the orientation flat face at the time of dry etching is disclosed by, for example, Japanese Laid-Open Patent Application No. 1-44038. According to this document, the position of the orientation flat surface of a wafer in a cassette is changed using a conical revolving member (see FIG. 30). According to this method, however, the positions of all wafers in the cassette are uniformly changed. On this account, for example, it is impossible to optionally change the position of a particular wafer in the cassette. In other words, being different from the present embodiment, the method disclosed by Japanese Laid-Open Patent Application No. 1-44038 does not make it possible to specify which processing device caused a defect, by differentiating the positions of wafers. In addition to the above, even if various methods of aligning notches and orientation flat surfaces have been proposed, all of these methods propose to align the notches or orientation flat surfaces in a single orientation. None of the methods disclose or indicate such a technical idea that only a particular wafer in the cassette is rotated in an optional orientation as described in the present embodiment.

Example 2

Of Position Change

Figure 10:
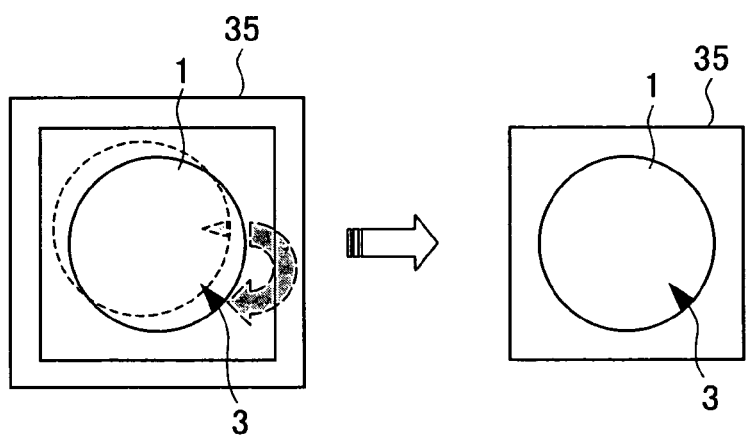
FIG. 10 shows an example 2 of position change.

Taking into account the productivity, it is preferable to shorten a time required for changing the position of the wafer 1. For this reason, notch aligning capability of the directly preceding processing device 13 may be utilized as shown in FIG. 10. For example, there are steps, such as line width measurement, to which not all wafers are necessarily subjected. In such a step, for example, only the first one of the wafers 1 in a cassette is measured or inspected. In this case, only the position of the notch 3 of the first wafer 1 is changed, unless the notch alignment of all wafers 1 is carried out again. If the first one of the wafers 1 is transported to the following processing device while the position of the notch 3 of that wafer 1 is kept intact, the position change of the present embodiment is achieved without performing the position change of the wafers 1.

For example, a film thickness measuring device measures the thickness of a film formed on a treatment object (by, for example, oxidation), in order to check if a desired thickness is achieved. Also, the film thickness measuring device measures the thickness after etching, in order to check if the film has been removed by the etching.

The thickness measurement is rarely carried out on all wafers 1. Usually the number of wafers 1 to be subjected to the measurement is one or two. This is because the measurement of a representative wafer is enough for high-quality manufacturing processes. In a case of automatic measurement, a predetermined pattern is searched on the wafer 1. Alignments are therefore carried out. To find a measurement point, the precision of the alignment is gradually increased. The details are discussed below.

First, a notch detector detects the notch 3, and the center of the wafer 1 is also detected. Then the wafer 1 is transported to the inside of a measuring device. Before the transportation, the orientation of the notch 3 is changed to a desired orientation (rough alignment 1). Then the alignment of the wafer 1 is performed (rough alignment 2). In doing so, since the pattern formed on the wafer 1 in this case is minute, a microscope in the measuring device is adjusted to low magnification. The rough alignment 2 is carried out as follows: first, coordinates are specified and a microscopic image around a measured point is roughly obtained. Since the measuring point has been recorded in the measuring device in advance, whether or not the obtained image corresponds to the recorded pattern is checked in reference to the measuring point. If the image does not correspond to the pattern, the measuring point is automatically found out from the surrounding area.

Thereafter, the magnification of the microscope is increased and the microscope focuses on a desired measuring point (fine alignment), so that the thickness of the film is measured. Also in this case, a pattern to be measured has been recorded as an image in advance. If the obtained image does not correspond to the pattern, the desired pattern is automatically found out from the surrounding area.

After the above-described measurement, the notch of the wafer 1 having been subjected to the measurement takes a predetermined orientation.

The orientation of the notch 3 after the measurement is set so as to be different from the notches 3 of the respective wafers 1 which are not subjected to the measurement, and the orientation of the notch 3 after the measurement is recorded. In this manner, the relative position change is achieved during the manufacturing process, without additionally performing the notch alignment. Since it takes few minutes to change the orientation of the notch 3, the position change is preferably carried out in a process involving alignments as above. This makes it possible to shorten the manufacturing time.

The alignment similar to the above is carried out in the line width measurement device. That is, a desired pattern (e.g. the line width after etching and the resist width after photolithography) is measured. It is therefore possible to carry out the above-described position change, also using this device.

Example 3

Of Position Change

Figure 11:
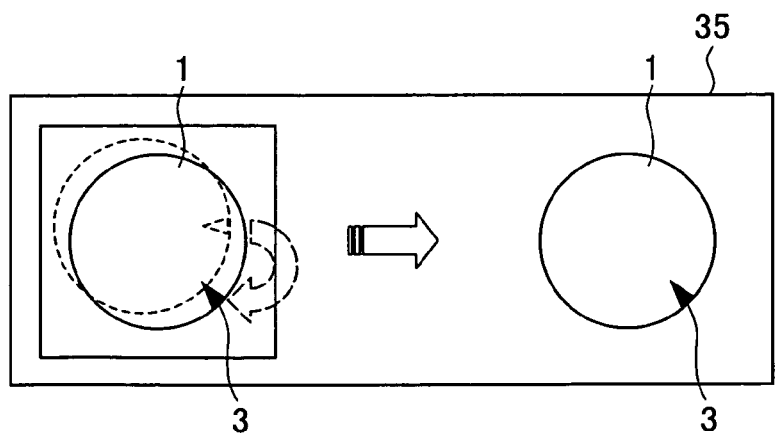
FIG. 11 shows an example 3 of position change.

FIG. 11 shows a case where the position change is carried out by a processing section 35 having notch alignment capability. For example, a dry etching device generally has such a notch alignment capability as to align the notches 3 in a single orientation. The position change in the present embodiment is achieved using the notch alignment capability.

For example, after aligning the notches in a single orientation, the position of a particular notch is changed using a timing belt or a stepping motor. In this case, either one of the following arrangements is preferable: the position of the notch of each wafer is changeable during the system construction of the device or the process recipe; or the orientation of the notch is optionally changeable in response to an instruction from the analyzing device.

Example 4

Of Position Change

Figure 12:
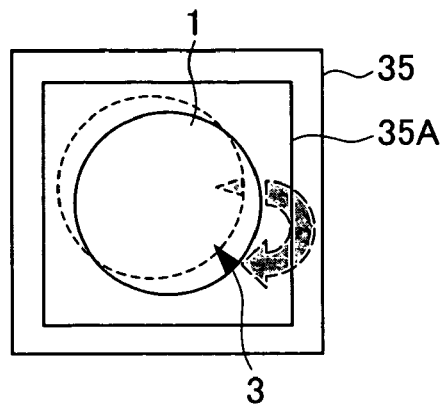
FIG. 12 shows an example 4 of position change.

FIG. 12 shows a case where the processing section 35 changes, by rotating a wafer stage 35A in a processing chamber of the processing section 35, the position of the notch 3 of the wafer 1 placed on the wafer stage 35A. For example, in a photo-resist applicator, the notch 3 is set at a desired position by rotating the wafer stage 35A, before the resist discharge. Thereafter the resist discharge starts, and for adjusting the film thickness, the wafer stage 35A is rotated. According to this arrangement, in a case of irregular resist discharge (e.g. adhesion of dust), the locations of defects on account of the irregularity are different from each other with respect to the position of the notch 3 of the wafer 1. This arrangement therefore makes it possible to achieve the position change of the present embodiment. A similar arrangement can be achieved in processing devices other than the photo-resist applicator, on condition that the processing device has a capability of rotating the wafer stage.

Example 5

Of Position Change

Figure 13:
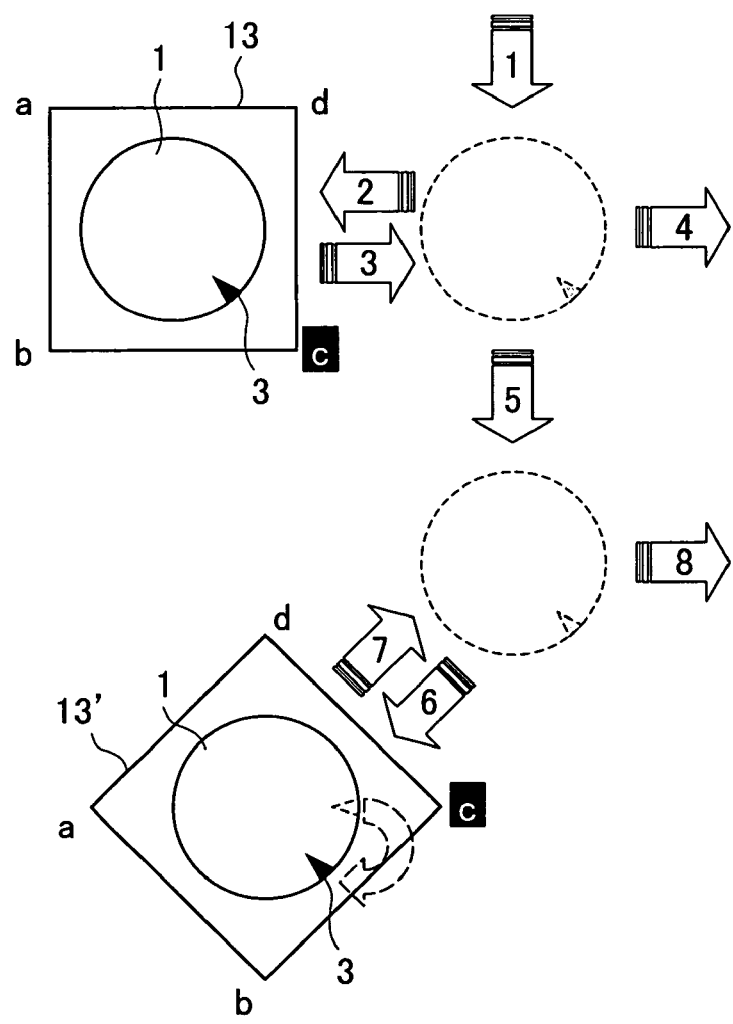
FIG. 13 shows an example 5 of position change.

FIG. 13 shows a case where the layout of the processing devices 13 and the transportation path are changed so that the notch position is optionally changeable without using a device having a notch alignment capability. In the example illustrated in the figure, processing devices 13 and 13' have identical processing capabilities, and the wafer 1 is processed by the processing devices 13 and 13'. In the processing device 13, the wafer 1 is processed in the order indicated by arrows 1, 2, 3, and 4 in the figure. In the processing device 13', the wafer 1 is processed in the order indicated by arrows 1, 5, 6, 7, and 8 in the figure.

In this case, while the notch 3 is in the c orientation in the processing device 13, the notch 3 in the processing device 13' is at an angle of 45° in comparison with the c orientation. That is, in this example, the position change section 32 changes the position thanks to the layout of the processing devices 13 and the transportation path.

In the present example, the processing devices 13 and 13' are the sheet-feed type so as not to use cassettes. However, the relative position change can be achieved also in a case where cassettes are used, if an entire-quantity process is not employed (e.g. the aforesaid measurement process is carried out) or only a wafer 1 in a development phase is subjected to a special process.

Example 6

Of Position Change

Figure 14:
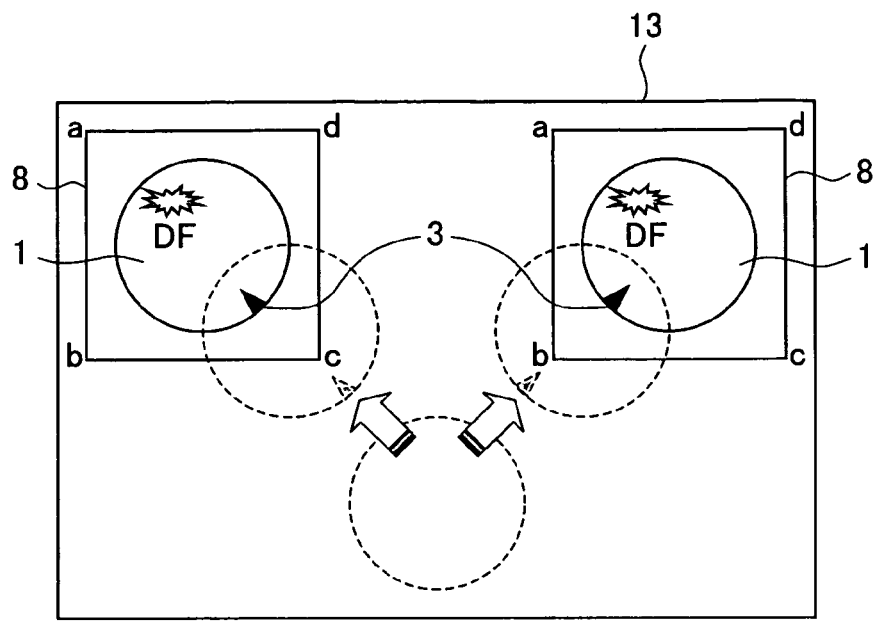
FIG. 14 shows an example 6 of position change.

FIG. 14 shows a case where the notch position is optionally changeable without using a device having a notch alignment capability, on account of an improved way of transfer of the wafer 1 in a processing device 13. In a processing device 13, sheet-feed chambers 8 as processing sections 35 are provided. To the chambers 8, the wafer 1 is transported by the transportation section 36, from different orientations. In the example illustrated in the figure, the wafer 1 is transported to the first chamber 8 from the c orientation in the figure. On the other hand, the wafer 1 is transported to the second chamber 8 from the b orientation in the figure. As a result, the notch 3 of the wafer 1 is relatively positioned differently in the respective chambers.

Provided that the first and second chambers 8 are liable to cause a defect DF in the a orientation, the wafer 1 processed in the first chamber 8 has a defect DF at an angle of 180° from the notch 3 in the clockwise orientation, while the wafer 1 processed in the second chamber 8 has a defect DF at an angle of 90° from the notch 3 in the clockwise orientation. In this case, the relationship between the location of the defect DF and the position of the notch 3 is uniquely determined in each wafer 1. On this account, the position change of the present embodiment can be achieved. That is, in the present example, the position change by the position change section 32 is achieved by optionally setting (i) the layout of the chambers 8 and (ii) from which orientations a treatment object is transported to the respective chambers 8.

Example 7

Of Position Change

Figure 15:
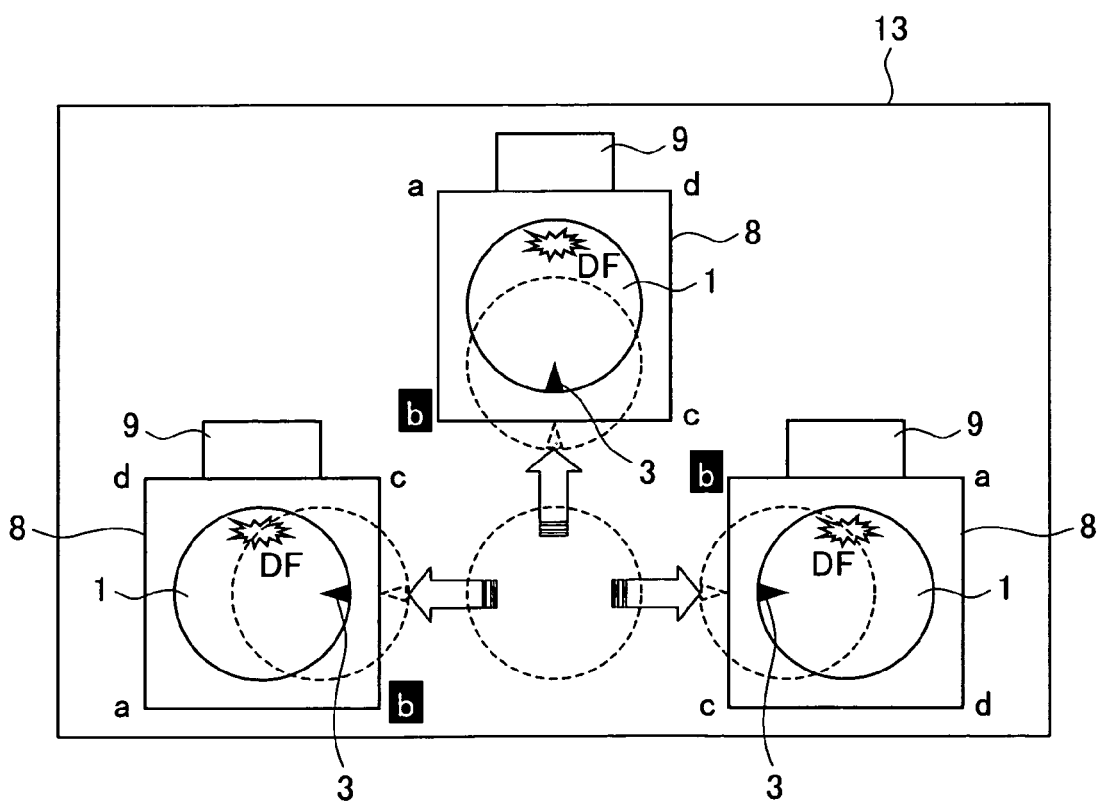
FIG. 15 shows an example 7 of position change.

FIG. 15 shows a case where, a part of the processing device is relatively changed with respect to the wafer 1 as a treatment object, so that the notch position is optionally changeable without using a device having a notch alignment capability.

The processing device 13 in this example has a plurality of chambers 8. In each chamber 8, a transportation outlet through which the wafer 1 is transported is provided on an identical side (side b-c in the example in the figure) of each chamber 8. Also, in the respective chambers 8, exhaust ports 8 are provided on different sides. In the example illustrated in the figure, the exhaust ports 9 are on the sides a-d, d-c, and b-a of the first, second, and third chambers 8, respectively.

According to the arrangement above, in the respective chambers 8, the relative positions of the notches 3 of the wafers 1 are different with respect to the discharge ports 9. For example, if a defect is liable to occur around the exhaust port 9 of the chamber 8, the positional relationship between a defect DF (e.g. a foreign matter adhered to the wafer 1) and the position of the notch 3 is different among the wafers 1. It is therefore possible to achieve the position change of the present embodiment. That is, in the present example, the position change by the position change section 32 is achieved by appropriately setting (i) the layout of the chambers 8 and (ii) from which orientations a treatment object is transported to the respective chambers 8, by the transportation section 36.

In a case where the processing device 13 has only one chamber 8, the process may be carried out as follows: first, factors which are liable to cause problems are memorized. For example, a gas inlet of the chamber 8 is at an angle of 90° with respect to the notch 3, while an exhaust outlet is at an angle of 180° with respect to the notch 3. Thereafter, if the inspection device 14 detects that a foreign matter locates at an angle of 90° with respect to the notch 3, it is possible to assume that the foreign matter be generated at the gas inlet of the processing device 13. In other words, the steps whose relative positions cannot be changed are regarded as "unchanged steps", and the analysis is carried out based on the above-described factors.

Example 8

Of Position Change

Figure 16:
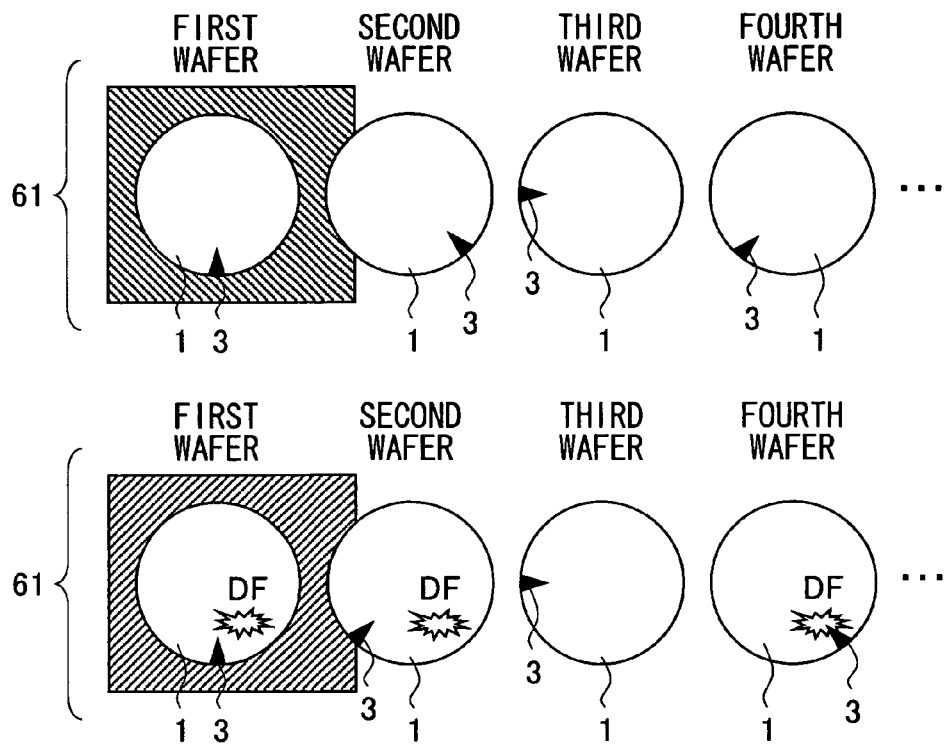
FIG. 16 shows an example 8 of position change.

FIG. 16 shows a case where there are processing device groups 61 each including sheet-feed processing devices 13, and the order of position change of the wafer 1 is different among the processing device groups 61. That is, a predetermined number of wafers 1 is regarded as one processing group, and the order of positions of the wafer 1 in each processing group is different among the processing device groups 61. With this, it is possible to specify in which processing device group 61 a defect occurred. Incidentally, a sheet-feed processing device subjects the wafers 1 to the process one by one.

In the example shown in the figure, in the first processing device group 61, the notch 3 of the first wafer 1 is on the lower side, the notch 3 of the second wafer 1 is on the lower right side, the notch 3 of the third wafer 1 is on the left side, and the notch 3 of the fourth wafer 1 is on the lower left side. These four wafers 1 constitute one processing group. The fifth wafer and the following wafers also constitute groups in a similar manner. In short, every four wafers form one processing group.

Similarly, in the second processing device group 61, the notch 3 of the first wafer 1 is on the lower side, the notch 3 of the second wafer 1 is on the lower left side, the notch 3 of the third wafer 1 is on the left side, and the notch 3 of the fourth wafer 1 is on the lower right side. As a result, the first and second processing device groups 61 are different from each other in terms of the order of the positions of the wafers 1. Because of this arrangement, it is possible to identify in which processing device group 61 (the second processing group 61 in the example shown in the figure) a defect DF occurred, in reference to the difference between the positions of the defect DF in the respective processing groups.

If the position of the notch 3 is uniquely determined with respect to each processing device 13, it is possible to identify in which processing device 13 a defect occurred. Meanwhile, as in the present example, identical processing devices 13 may be grouped as a processing device group 61, so that a combination of the positions are shared between those processing devices 13.

Grasping in which processing device group 61 a defect occurred is advantageous in that even if some of the wafers 1 have no defect, data of a defect peculiar to the processing device group 61 is compensated by other processes in the same processing device group 61. That is to say, in actual manufacture of wafers 1, a defect peculiar to the processing device may not occur. In the example illustrated in FIG. 16, if a defect does not occur in the third wafer in one processing device 13 of the processing device group 61, the accuracy of the assumption of the causal device decreases. Also, the accuracy of the assumption further decreases in a case where a defect does not occur in the second and fourth wafers in another processing device 13 of the same processing device group 61. Now, assume that such incompletely-occurring defects are defects of the same processing device group, and the defects on the first wafers, second wafers, and third wafers and so on are collectively regarded as a defect of the first wafers, a defect of the second wafers, and so on. In such a case, it seems as if the defects occur on all of the first to fourth wafers, and hence the accuracy of the assumption increases. It is noted that, while the locations of defects peculiar to one processing device group are roughly overlapped with each other, these locations do not overlap with the locations of defects of another processing device group. Such not-overlapping defects are assumed as those of another processing device group, and are independently overlapped with one another. By the way, the defects of the first wafers, second wafers, third wafers and so on of one processing device may be collectively regarded as a defect of the first wafers, a defect of the second wafers, and so on, as in the assumption above.

Furthermore, since the occurrence of a defect is recognized in units of processing device groups 61, a countermeasure for defect reduction may be taken not only to a processing device 13 causing the defect but also to other processing devices 13 in the same processing device group 61.

Example 9

Of Position Change

Figure 17:
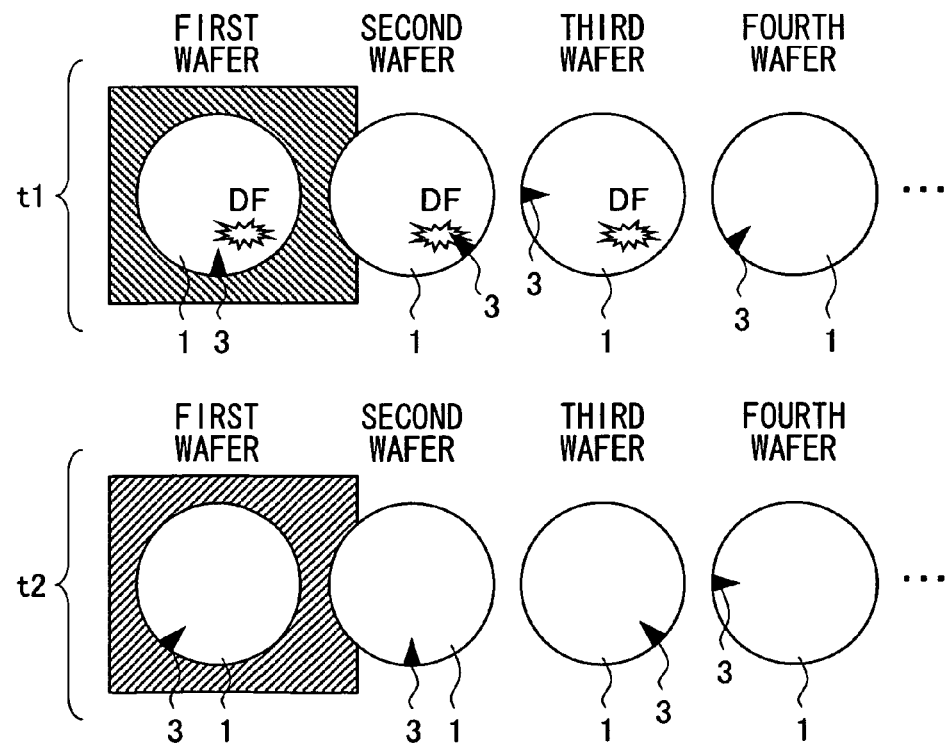
FIG. 17 shows an example 9 of position change.

FIG. 17 shows a case where the order of position change of the wafer 1 in a sheet-feed processing device 13 is varied over time. That is, a predetermined number of wafers 1 is grouped as a processing group, and the order of the positions of the wafer 1 is set so as to be different among time periods. This makes it possible to specify when the defect occurred.

In the example shown in the figure, in a first time period t1, the notch of the first wafer 1 is on the lower side, the notch 3 of the second wafer 1 is on the lower right side, the notch 3 of the third wafer 1 is on the left side, and the notch 3 of the fourth wafer 1 is on the lower left side. These four wafers 1 constitute one processing group. The fifth wafer and the following wafers also constitute groups in a similar manner. In short, every four wafers form one processing group.

Similarly, in the second time period t2, the notch 3 of the first wafer 1 is on the lower left side, the notch 3 of the second wafer 1 is on the lower side, the notch 3 of the third wafer 1 is on the lower right side, and the notch of the fourth wafer 1 is on the left side. As a result, the order of the positions of the wafers 1 in each processing group is different between the first and second time periods t1 and t2. For example, it is possible to identify in which time period (time period t1 in the example shown in the figure) a defect DF occurred, by referring to the change in the locations of the defect DF in each processing group. Because of the above, it is possible to analyze the relation between (i) events such as a maintenance time and a trouble occurring time and (i) a period when the defect occurs.

Example 10

Of Position Change

Figure 18:
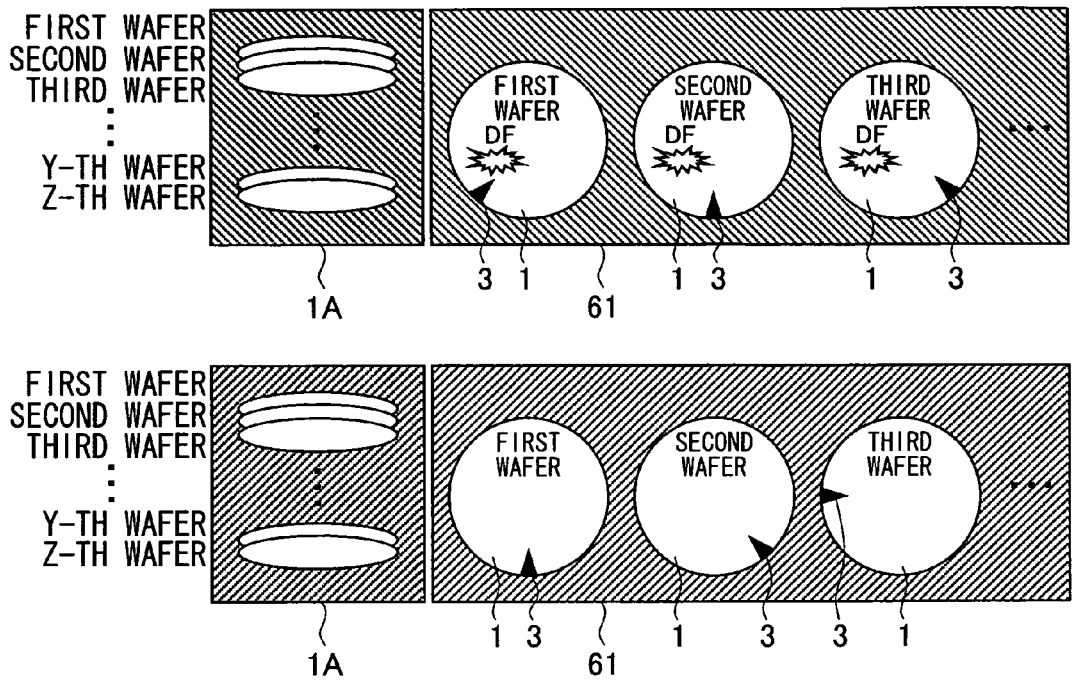
FIG. 18 shows an example 10 of position change.

FIG. 18 shows a case where there are processing device groups 61 each including processing devices 13 as batch devices, and a combination of the positions of wafers 1 in a cassette 1A is different among the processing device groups 61. It is possible in this case to specify in which processing device group 61 a defect occurred. It is noted that a batch device subjects a plurality of wafers 1 to a process at once.

In the example shown in the figure, in the first processing device group 1, the notch 3 of the first wafer 1 is on the lower left side, the notch 3 of the second wafer 1 is on the lower side, and the notch 3 of the third wafer 1 is on the lower right side. The positions of the notches of the fourth to Z-th wafers 1 are set in a similar manner. Also, in the second processing device group 61, the notch 3 of the first wafer 1 is on the lower left side, the notch 3 of the second wafer 1 is on the lower side, and the notch 3 of the third wafer 1 is on the lower right side. The positions of the notches of the fourth to Z-th wafers 1 are set in a similar manner. Because of this arrangement, the order of the positions of the wafers 1 in the cassette 1A is different between the first and second processing device groups 61. For example, it is possible to identify in which processing device group 61 (first processing device group 61 in the example illustrated in the figure) the defect DF occurred, in reference to the order of the locations of the defect DF in the cassette 1A.

If the position of the notch 3 is uniquely determined with respect to each processing device 13, it is possible to identify in which processing device 13 a defect occurs. Meanwhile, as in the present example, identical processing devices 13 may be grouped as a processing device group 61, so that a combination of the positions are shared between those processing devices 13.

Since the example 8 has already described why it is advantageous to identify the occurrence of a defect in units of processing device groups 61, the reason is omitted here.

As in the case of sheet-feed devices, the position of the notch of the wafer on the top of a vertical furnace may be different among batches. However, the position change of the present embodiment can be achieved in a single batch, by optionally changing the positions of the notches 3 of the wafers 1 in the cassette 1A as above.

Example 11

Of Position Change

Figure 19:
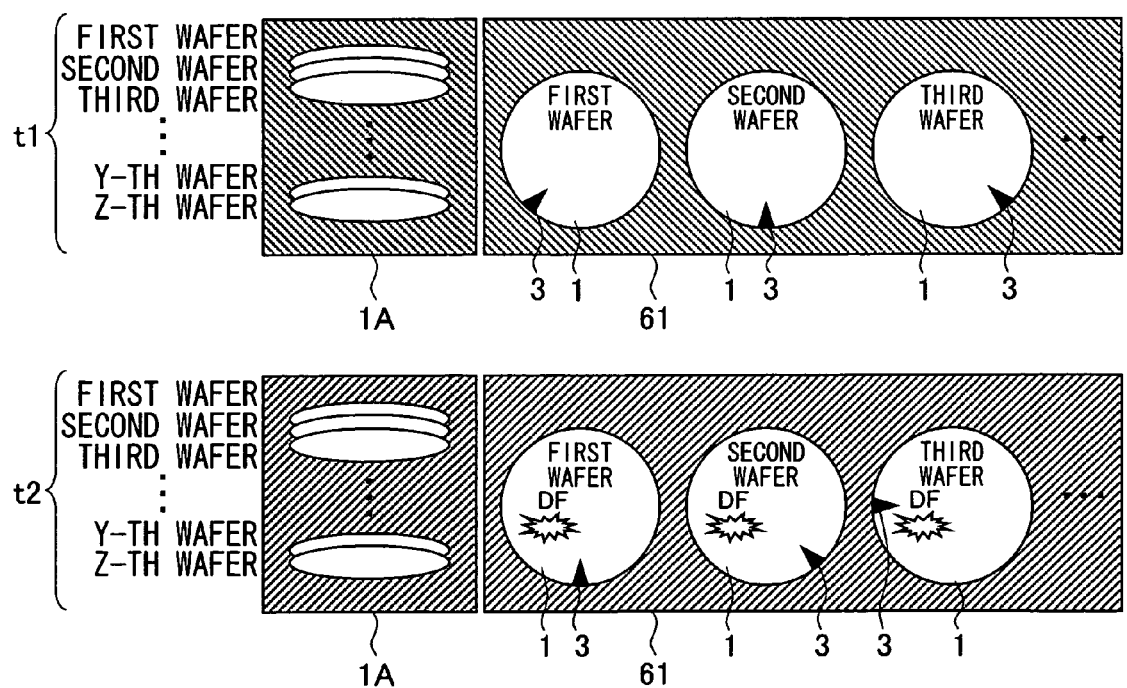
FIG. 19 shows an example 11 of position change.

FIG. 19 shows a case where, in a processing device 13 functioning as a batch device, a combination of positions of wafers 1 in a cassette 1A is varied over time. This makes it possible to specify when a defect occurred.

In the example illustrated in the figure, in a first time period t1, the notch 3 of the first wafer 1 is on the lower left side, the notch 3 of the second wafer 1 is on the lower side, and the notch 3 of the third wafer 1 is on the lower right side. The notches 3 of the fourth to Z-th wafers are similarly arranged.

Also, in a second time period t2, the notch 3 of the first wafer 1 is on the lower side, the notch 3 of the second wafer 1 is on the lower right side, and the notch 3 of the third wafer 1 is on the left side. The notches 3 of the fourth to Z-th wafers are similarly arranged. With this, the order of the positions of the wafers 1 in the respective slots is different between the first and second time periods t1 and t2. For example, it is possible to specify in which time period (second time period t2 in the example shown in the figure) a defect DF occurred in the cassette 1A. Therefore, it is possible to analyze the relation between (i) events such as a maintenance time and a trouble occurring time and (i) a period when the defect occurs.

Example 12

Of Position Change

Figure 20:
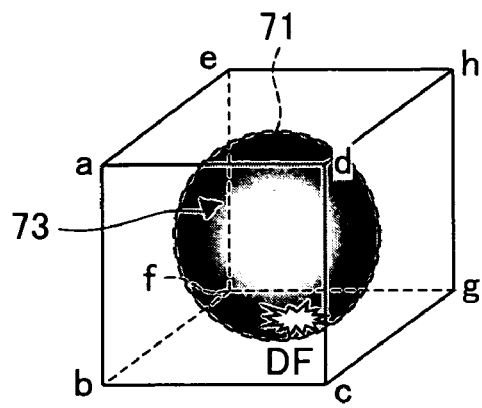
FIGS. 20(a) and 20(b) show an example 12 of position change.
Figure 20:
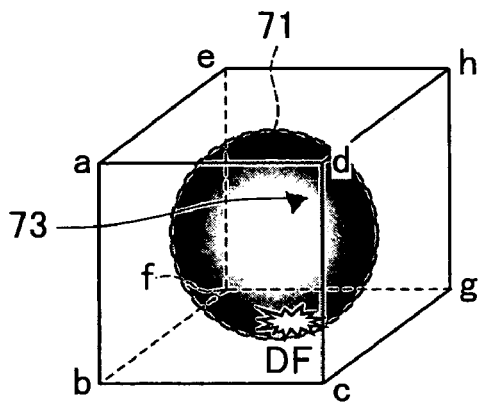

FIGS. 20(a) and 20(b) show a case where the treatment object is a sphere 71. Even if the treatment object is a sphere 71, the position change of the present embodiment can be achieved by providing a reference point 73 on the sphere 71, and differentiating the reference point 73 between the processing devices 13. In the present case, the difference between the reference points corresponds to the difference between FIGS. 20(*a*) and 20(*b*). That is, even when the treatment object is a sphere 71, it is possible to specify a processing device 13, a processing device group 61, or a processing time period in which the defect occurs, by performing the process similar to those in Examples 1-11. The treatment object is a sphere 71 in the present example. Alternatively, the treatment object may have any three-dimensional structures, such as a rectangular solid, tetrahedron, and other complex three-dimensional structures.

(Specifying Processing Step)

The descriptions above relate to examples for specifying in which processing device 13 a defect occurred. Meanwhile, a defect may occur during the transportation of a treatment object. That is, for example, through the transportation from one processing device 13 to the next processing device 13, the treatment object may be damaged or a foreign matter may be attached to the object, because the transportation device 15 holds or transfers the treatment object.

Figure 21:
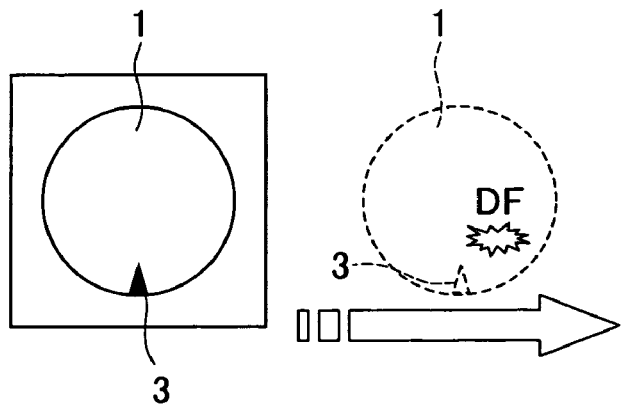
FIG. 21 shows a case where a defect occurs while a wafer is transported.
Figure 21:
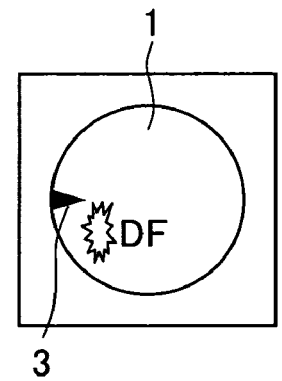

FIG. 21 shows a case where a defect occurs during the transportation of a wafer 1 from a processing device 13 that performs a Y-th process to a processing device 13 that performs a Z-th process. During the transportation, the position of the notch 3 of the wafer 1 is identical with the position in the Y-th process. That is, the analyzing process section 23 recognizes that a defect occurs either in a processing device 13 specified thanks to the position of the notch 3 or in the transportation from the processing device 13 to the next processing device 13.

Alternatively, it is possible to determine whether or not the transportation device 15 caused a defect, if the transportation device 15 is regarded as an independent processing device and the position of the notch 3 is changed also in the transportation device 15.

(Example of Recognition of Defect)

Figure 22:
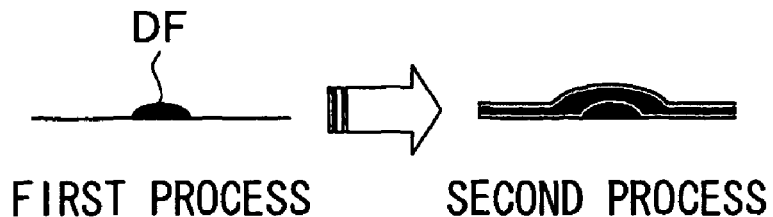
FIGS. 22(a) and 22(b) show a case where the film formation and etching are performed after the occurrence of a defect.
Figure 22:
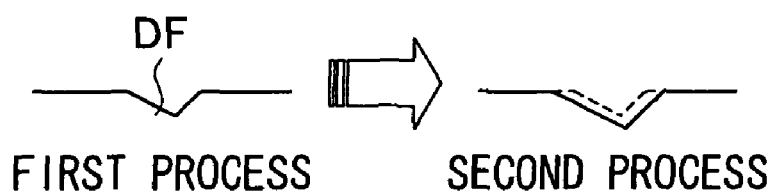

FIG. 22(*a*) illustrates a case where a defect DF occurs because a foreign matter is attached in a first process, and the formation of a film is carried out in a second process. The defect DF occurs in the first process on account of the adhesion of the foreign matter. At this point, however, the defect is relatively minor and negligible. In the following second process, the defect becomes obvious on account of the formation of the film around the defect.

In a similar manner, FIG. 22(*b*) shows a case where a defect DF occurs on account of a damage caused in a first process, and then etching is carried out in a second process. The defect DF occurs in the first process on account of the damage. At this point, however, the defect is relatively minor and negligible. In the following second process, the defect becomes obvious because the defect DF is enlarged on account of the etching.

In the aforesaid cases, for example, a system that detects the occurrence of a defect by appearance observation in each process may erroneously recognize that the defect was caused in the process where the defect became obvious. The inspection and improvement of the processing device 13 where the defect became obvious are waste of time and cost.

In the meanwhile, according to the defect analysis system of the present embodiment, the processing device that caused a defect is specified based on the location of the occurrence of the defect. It is therefore possible to specify the process where the causal defect occurred, in place of the process where the defect became obvious. On this account, the inspection and improvement are properly carried out. Incidentally, since a foreign matter generated in a highly-clean manufacturing device tends to be miniature, it may be effective to cause the defect to be obvious as above.

Figure 23:
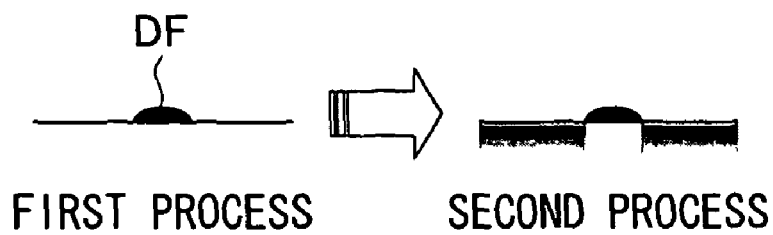
FIG. 23 shows a case where injection is carried out after the occurrence of the defect.

FIG. 23 shows a case where a defect DF occurs because a foreign matter adheres in a first process, and injection is carried out in the following second process. In this case, although the defect does not physically become obvious in the second process, the defect occurred in the first process functions as an obstruction to the injection, so that the defect became evident.

In such a case where the inspection by a defect inspection machine is difficult, the inspection may be carried out in such a manner that the electric property is measured and the defect is assumed based on the measured electric property. In case of semiconductor apparatuses, the measurement of the electric property is preferably performed before the dicing is carried out. If the measurement is carried out after the dicing into chips is carried out, the measurement may be performed after recording where a chip was located on the wafer.

(Example of Property Measurement)

Figure 24:
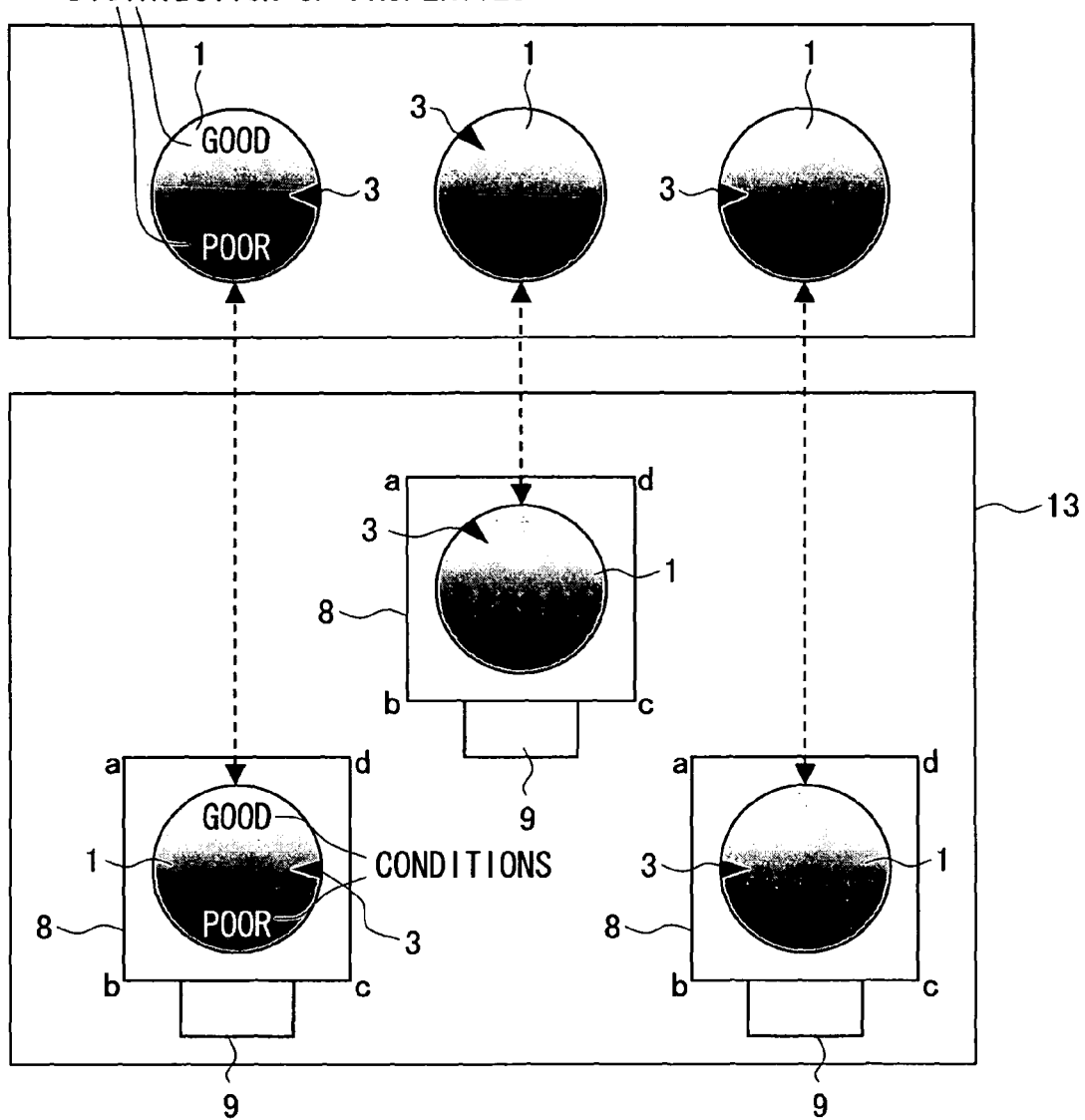
FIG. 24 shows an example of inspecting a device or condition which is not suitable for the manufacture.

FIG. 24 shows an example of inspecting which device or condition is not suitable for the manufacture. In this example, the distribution of properties of wafers 1, which are measured by an electric property inspection device 14, is relatively different from the positions of the notches 3, and the relative positional relation relates to the positions of the notches 3 of the wafers 1 in the Y-th process. This result indicates that the bias in the distribution of the electric properties measured by the electric property inspection device 14 is generated because either the Y-th processing device 13 or the condition is inappropriate.

In the present example, the location of the exhaust port 9 in each chamber 8 of the Y-th processing device 13 corresponds to the distribution of defects of the wafer 1, which is measured by the electric property inspection device 14, and hence it is found that the inconsistency in the condition around the exhaust port 9 caused the poor electric property. In this manner, in the manufacture of semiconductor wafers, it is possible to inspect which processing device 13 or condition is inappropriate to the manufacture, and to promptly carry out the improvement.

On the other hand, the performances of products, prototypes or the like can be improved by (i) specifying a quality part of the wafer 1 or a processing device 13 that produces a high-performance part, and (ii) inspecting and feeding back the conditions of them.

(Details of Wafer Position Change)

The following discusses the details of the position change of the wafer 1 by the position change section 32. First, how the position of the notch 3 is changed by rotating the wafer 1 is described. The determination of the position of the notch 3 is carried out not by detecting the resultant position of the notch 3 but by memorizing to what extent (angle) the notch 3 is rotated from the original position of the notch 3, which position has been detected.

First, on a rotatable notch detection stage, the wafer 1 is placed so that the rotational axis of the stage overlaps the center of the wafer 1. A laser beam is applied to the end face of the wafer 1, and a sensor receives the reflected light beam. As the wafer 1 rotates, the orientation of the reflected light changes only when the laser beam is applied to the notch. Therefore the sensor does not receive the laser light only when the laser light is applied to the notch. This position where the sensor does not receive the light is recognized as the position of the notch 3. From this position, the wafer 1 is further rotated for $+\alpha°$ or $-\alpha°$. The angle $\alpha°$ is predetermined, and may be different among the wafers 1. The relative position change is achieved by transporting, to the processing section 35, the wafer 1 which has been rotated so that the orientation of the notch 3 has been changed.

On the other hand, the detection of the notch 3 may be achieved in such a manner that. A laser beam is applied from above onto the wafer edge, and a sensor provided below the wafer 1 receives the laser beam only when the notch 3 is above the sensor, while the laser beam is blocked by the wafer edge if the notch 3 is not above the sensor. Meanwhile, in a case where the wafer stage of the processing section 35 can be rotated to an optional orientation, the position change may be carried out as follows: first, the position change section 32 stops the rotation of the notch detection stage if the notch 3 is detected, and the wafer 1 is transported to the processing section 35 while the position of the notch 3 is unchanged. Thereafter, the wafer stage of the processing section 35 is rotated for $+\alpha°$ or $-\alpha°$.

Now, the following discusses a case where the position of the notch 3 is changed by horizontally moving the wafer 1. When the transportation section 36 transports the wafer 1 to the processing section 35, the position of the wafer 1 is changed by controlling the moving distance of the transportation arm. The information regarding the position is stored in the position memory section 34. Provided that the center of the wafer processing stage is regarded as a normal position, the transportation arm is moved for a mm towards the inside or outside of the processing chamber, and the wafer 1 is placed on the processing stage. In this manner, the position change by the horizontal movement is achieved. (The position change may be achieved by rightward movement, leftward movement, or a combination thereof.) In a case where the processing stage is far smaller than the wafer 1 and hence the stage cannot adsorb and hold the wafer 1, the wafer 1 may be dropped in the processing chamber, as a result of the movement. In such a case, the position change is achieved by moving the processing stage, if the processing stage can be horizontally moved.

(Example of Processing Device Whose Position Cannot be Changed)

Basically, in the manufacture of semiconductor wafers, for example, there are almost no processing devices 13 in which the position change is not feasible. An example where the position change is not feasible is a photo-exposure process. In the photo-exposure process, the position change causes the misalignment of a foundation pattern, because the exposure must be carried out in line with the pattern. In such a case, even though the photo mask cannot change its relative position with respect to the wafer, the position change can be achieved by rotating the light source or rotating the processing stage (without changing the relative positions of the wafer and mask).

If the position change is impossible in a process by any means, the inspection and analysis may be performed after that process (and before the next process where the relative position change is impossible).

(Implementation in Software)

The analyzing process section 23 and the position change setting section 25 of the analyzing device 12 of the above-described embodiment are implemented in such a manner that computing means such as a CPU executes a program stored in storage means such as a ROM (Read Only Memory) and RAM so as to control input means such as a keyboard, output means such as a display, and a communication means such as an interface circuit. Therefore, the functions and processes of the analyzing device 12 of the present embodiment are realized only by causing a computer including the aforesaid means to read a storage medium storing the program, so as to execute the program. Moreover, if the program is stored in a removable storage medium, the functions and processes are realized on any computers.

Such a computer program storage medium may be a memory (not shown), such as a ROM, so that the process is executable on a microcomputer. Alternatively, a program medium may be used which can be read by inserting the storage medium in an external storage device (program reader device; not shown).

In addition, in either of the cases, it is preferable if the contained program is accessible to a microprocessor which will execute the program. Further, it is preferable if the program is read, and the program is then downloaded to a program storage area of a microcomputer where the program is executed. Assume that the program for download is stored in a main body device in advance.

In addition, the program medium is a storage medium arranged so that it can be separated from the main body. Examples of such a program medium include a tape, such as a magnetic tape and a cassette tape; a magnetic disk, such as a flexible disk and a hard disk; a disc, such as a CD/MO/MD/DVD; a card, such as an IC card (inclusive of a memory card); and a semiconductor memory, such as a mask ROM, an EPROM (erasable programmable read only memory), an EEPROM (electrically erasable programmable read only memory), or a flash ROM. All these storage media hold a program in a fixed manner.

Alternatively, if a system can be constructed which can connects to the Internet or other communications network, it is preferable if the program medium is a storage medium carrying the program in a flowing manner as in the downloading of a program over the communications network.

Further, when the program is downloaded over a communications network in this manner, it is preferable if the program for download is stored in a main body device in advance or installed from another storage medium.

SUMMARY OF PRESENT INVENTION

As described above, a manufacturing inspection/analysis system includes: processing devices each subjecting at least one treatment object to a predetermined process; an inspection device that detects bias in distribution of processing qualities of said at least one treatment object, after the processing devices perform the process; and an analyzing device that performs an analyzing process so as to specify in which one of the processing devices or one of processing device groups the bias is generated, and at least one of the processing devices including a position change section that changes, at a time of the predetermined process, a position of said at least one treatment object so as to cause the position to correspond to a predetermined position which is in conformity to said at least one treatment object, and the analyzing device including an analyzing process section that carries out the analyzing process in accordance with (i) positional information of said at least one treatment object in each of the processing devices and (ii) processing quality distribution bias information detected by the inspection device.

The above-described manufacturing inspection/analysis system may be arranged in such a manner that the analyzing device further includes a position change setting section that instructs the position change section of each of the processing devices to set the position of said at least one treatment object to be different among the processing devices or the processing device groups.

According to the arrangement above, the position change setting section of the analyzing device causes the position change to be different among the processing devices or processing device groups. This allows the alterations in the manufacturing process, because the position change is appropriately set on the analyzing device side.

The above-described manufacturing inspection/analysis system may be arranged in such a manner that the inspection device is an appearance inspection device that detects the bias by inspecting appearance of said at least one treatment object.

According to the arrangement above, the appearance inspection device detects the bias in distribution of processing qualities. It is therefore possible to precisely detect the bias which is detectable by appearances.

The above-described manufacturing inspection/analysis system may be arranged in such a manner that the inspection device is an electric property evaluation device that detects the bias by inspecting an electric property of said at least one treatment object.

According to the arrangement above, the electric property evaluation device detects the bias in distribution of processing qualities. It is therefore possible to properly detect a defect which is not detectable by appearances.

The above-described manufacturing inspection/analysis system may be arranged in such a manner that the position change section changes the position of said at least one treatment object by rotating said at least one treatment object.

According to the arrangement above, the position of the treatment object is changed by rotating the treatment object. In this case, there are a lot of variations of the position change, while the center of the treatment object does not move so much as a result of the position change. It is therefore possible to adopt a relatively small stage for processes carried out by the processing devices.

The above-described manufacturing inspection/analysis system may be arranged in such a manner that the position change section changes the position of said at least one treatment object by horizontally moving said at least one treatment object.

According to the arrangement above, the position of the treatment object is changed by horizontally moving the treatment object. It is therefore possible to change the position of a defect by changing the position of the treatment object, even if the defect is shaped like a concentric circle around the center of the treatment object.

The above-described manufacturing inspection/analysis system may be arranged in such a manner that said at least one treatment object is a flat plate, and the position change section changes the position of said at least one treatment object by turning over said at least one treatment object.

According to the arrangement above, the position of the treatment object is changed by turning over the treatment object. In this case, there are a lot of variations of the position change, while the center of the treatment object does not move so much as a result of the position change. It is therefore possible to adopt a relatively small stage for processes carried out by the processing devices.

The above-described manufacturing inspection/analysis system may be arranged in such a manner that the position change section changes the position of said at least one treatment object outside a processing section, of at lest one of the processing devices, where said at least one treatment object is actually subjected to the predetermined process.

According to the arrangement above, the position of the treatment object is changed outside the processing section. It is therefore possible to perform the aforesaid position change in a processing device in which the position of a treatment object cannot be changed.

The above-described manufacturing inspection/analysis system may be arranged in such a manner that the position change section changes the position of said at least one treatment object inside a processing section, of each of the processing devices, where said at least one treatment object is actually subjected to the predetermined process.

According to this arrangement, the position of the treatment object is changed inside the processing section. On this account, the position change section may be means that changes the position of the object in the processing section.

The above-described manufacturing inspection/analysis system may be arranged in such a manner that the position change section is realized in each of the processing devices thanks to a positional relationship between a processing device and a directly preceding processing device, and the position change section changes the position of said at least one treatment object on account of transportation of the treatment object from the directly preceding processing device.

According to this arrangement, the position of the treatment object is changed by modifying a positional relationship between one processing device and the processing device that performs a process immediately before said one processing device performs a process. That is, the position change is achieved by modifying the layout of the processing devices. On this account, it is unnecessary to provide an ad-hoc arrangement for the position change of the treatment object.

The above-described manufacturing inspection/analysis system may be arranged in such a manner that at least one of the processing devices includes: processing sections each of which actually subjects said at least one treatment object to the predetermined process; and a transportation section that transports said at least one treatment object to the processing sections, and on account of the transportation section, said at least one treatment object is transported to the respective processing sections from different directions, so that the position change section is realized.

According to the arrangement above, a plurality of processing sections are provided in the processing device. By the transportation section, the treatment object is transported to the processing sections, from different directions. On this account, the position of the treatment object is changed in each of the processing sections. Therefore, since the position change is achieved by modifying the layout of processing sections, it is unnecessary to provide an ad-hoc arrangement for the position change of the treatment object.

The above-described manufacturing inspection/analysis system may be arranged in such a manner that said at least one treatment object is classified into processing groups, and the position change setting section causes a combination of positions of those treatment objects in one processing group to be different among the processing devices or the processing device groups.

According the this arrangement, a combination of the positions of the treatment objects in one processing group are different among the processing devices or the processing device groups. This makes it possible to properly perform the analyzing process by the analyzing process section, with reference to the positions of the treatment objects in the processing group. It becomes also possible to specify in which processing device or processing device group the process is carried out.

The above-described manufacturing inspection/analysis system may be arranged in such a manner that the position change setting section changes the combination, in accordance with a time period.

According to this arrangement, the combination of the positions of the treatment objects in the processing group is changed over time. It is therefore possible to specify in which time period the process is performed, in reference to the positions of the treatment objects in the processing group.

The above-described manufacturing inspection/analysis system may be arranged in such a manner that, in accordance with setting performed by the position change setting section, the position change section changes positions of some of said at least one treatment object, which are stored in a treatment object transportation member.

According to this arrangement, the position change is achieved by changing the position of the treatment object stored in the treatment object transportation member. It is therefore possible to properly perform the position change, even if the processing section in the processing device does not have means for changing the position of the treatment object.

The above-described manufacturing inspection/analysis system may be arranged in such a manner that said at least one treatment object is either one of a flat plate as a semiconductor wafer, a glass plate, and a resin plate.

According to this arrangement, the system can be used for manufacturing semiconductor wafers and other products shaped like a flat plate.

The above-described manufacturing inspection/analysis system may be arranged in such a manner that said at least one treatment object has a three-dimensional structure.

According to this arrangement, since the treatment object has a three-dimensional structure, the system can be used for manufacturing treatment objects with various shapes.

The above-described manufacturing inspection/analysis system may be arranged in such a manner that the processing devices are at least one of: a film forming device, a heat treatment device, an injection device, an etching device, a polishing device, an applicator device, an exposing device, a developing device, a washing device, a cutting device, an adhesion device, a joining device, a film thickness measurement device, a line width measurement device, and an alignment checking device.

According to this arrangement, the processing devices are, for example, those necessary for the manufacture of semiconductor wafers. It is therefore possible to use the system for manufacturing semiconductor wafers.

The above-described manufacturing inspection/analysis system may be arranged in such a manner that at least one of the processing devices is a transportation device that transports said at least one treatment object from and/or to another processing device.

According to this arrangement, in a case where bias in distribution of processing qualities, e.g. a defect, of the treatment object is generated in a transportation device, it is possible to specify in which transportation device the bias is generated.

An analyzing device of the present invention is provided in the above-described manufacturing inspection/analysis system of the present invention.

According to this arrangement, it is possible to provide the analyzing device that makes it possible to properly specify, during the process of manufacture of the treatment object, which processing device or processing device group caused the bias in distribution of processing qualities, without performing processes such as attaching, to the treatment object, information regarding processing devices which have conducted processes.

The manufacturing inspection/analysis system may perform the steps of: (i) performing a desired first process after placing a treatment object; (ii) performing appearance inspection after the process; and (iii) storing the information of the appearance inspection, and further perform the steps of: (iv) before the process, optionally changing the position of the treatment object relative to the process; (v) memorizing the relationship between the process and the relative position; (vi) analyzing the relationship between the position of the treatment object and the appearance inspection; (vii) memorizing the relationship in the step (vi); and (viii) analyzing a similar relationship of another treatment object.

The aforesaid manufacturing inspection/analysis system, which is a measurement/analysis system performing the steps of: (i) performing a desired first process after placing a treatment object; (ii) performing an electric measurement after the process; and (iii) memorizing the information regarding the electric measurement, may further perform the steps of: (iv) before the process, optionally changing the position of the treatment object relative to the process; (v) memorizing the relationship between the process and the relative position; (vi) analyzing the relationship between the position of the treatment object and the electric measurement; (vii) memorizing the relationship in the step (vi); and (viii) analyzing a similar relationship of another treatment object.

The aforesaid manufacturing inspection/analysis system may be arranged such that the inspection and measurement may be carried out immediately after the first process of the treatment object.

The aforesaid manufacturing inspection/analysis system may perform a second process which involves one or more relative position change performed between the first process and the inspection and measurement, and a step of memorizing the position after the change.

The aforesaid manufacturing inspection/analysis system may be arranged such that the inspection, measurement, and analysis are performed once in the process of product manufacture or the process of manufacture of a material for study, experiment, research, or monitoring.

The aforesaid manufacturing inspection/analysis system may be arranged such that one of the inspection, measurement, and analysis or a combination thereof is performed more than once in the process of product manufacture or the process of manufacture of a material for study, experiment, research, or monitoring.

The aforesaid manufacturing inspection/analysis system may be arranged such that a relationship between the positions of treatment objects in the first process may be different from a relationship among treatment objects in the second process.

The aforesaid manufacturing inspection/analysis system may be arranged such that the treatment object is a flat plate like a semiconductor plate, and the position of the object relative to the process is changed by optionally changing the horizontal rotation angle in reference to a reference point such as an orientation flat surface and a notch.

The aforesaid manufacturing inspection/analysis system may be arranged such that the treatment object is a flat plate like a semiconductor plate, and the position of the object relative to the process is changed by moving the plate. The movement excludes horizontal rotation.

The aforesaid manufacturing inspection/analysis system may be arranged such that the treatment object is a flat plate like a semiconductor plate, and the position of the object relative to the process is changed by turning over the flat plate.

The aforesaid manufacturing inspection/analysis system may be arranged such that the treatment object is a flat plate like a semiconductor plate, and the position of the object relative to the process is changed by performing at least one of the aforesaid methods or a combination thereof.

The aforesaid manufacturing inspection/analysis system may be arranged such that the position change relative to the first process is carried out using an alignment device which is outside a device that subjects the treatment object to a process.

The aforesaid manufacturing inspection/analysis system may be arranged such that the position change relative to the first process is carried out using an alignment device which is inside a device that subjects the treatment object to a process.

The aforesaid manufacturing inspection/analysis system may be arranged such that the position change relative to the first process is carried out by transporting the treatment object in the processing device, without using a device for aligning the treatment object.

The aforesaid manufacturing inspection/analysis system may be arranged such that the position change relative to the first process is carried out by changing the position by handing over the treatment object in the processing device, so as not to use a device for aligning the treatment object.

The aforesaid manufacturing inspection/analysis system may be arranged such that the position change relative to the first process is carried out by changing the position of the processing device relative to the treatment object, so as not to use an device for aligning the treatment object.

The aforesaid manufacturing inspection/analysis system may be a manufacturing device, product manufacturing factory, plant, and a production line for experiments, study, research, and monitoring, which adopt the aforesaid layout. Alternatively, manufacture or production may be performed there.

The aforesaid manufacturing inspection/analysis system may be arranged such that, in each sheet-feed device, the position relative to the first process is fixed at an optional position, or in each device group, the position is fixed at an optional position. Alternatively, a combination of these arrangements may be used.

The aforesaid manufacturing inspection/analysis system may be arranged such that, in each sheet-feed device, the position relative to the first process is optionally varied over time, or in each device group, the position is optionally varied over time. Alternatively, a combination of these arrangements may be used.

The aforesaid manufacturing inspection/analysis system may be arranged such that, in a device that subjects a plurality of treatment objects to a process at once, a position relative to the first process optionally changes a position of one or more treatment object in each device or each device group.

The aforesaid manufacturing inspection/analysis system may be arranged such that, in a device that subjects a plurality of treatment objects to a process at once, a position relative to the first process optionally changes a position of one or more treatment object in each device or each device group over time.

The aforesaid manufacturing inspection/analysis system may be arranged such that, in another one or more second processes performed between the process for the treatment object and the inspection and measurement, a foreign matter or defect is physically increased in size.

The aforesaid manufacturing inspection/analysis system may be arranged such that, another one or more second processes performed between the process for the treatment object and the inspection and measurement is a film formation or etching, in particular.

The aforesaid manufacturing inspection/analysis system may be arranged such that, which device or condition is not suitable for the manufacture is checked using the inspection/measurement/analysis system, and the result is fed back.

The aforesaid manufacturing inspection/analysis system may be arranged such that, which device or condition is suitable for the manufacture is checked using the inspection/measurement/analysis system, and the result is fed back.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

What is claimed is:

1. A manufacturing inspection/analysis system, comprising:
a plurality of processing devices, each of the plurality of processing devices configured to subject at least one treatment object to a manufacturing process, each of the plurality of processing devices including a position change section configured to change a position of the at least one treatment object to a set position, wherein the set position is different for each processing device or each processing device group;
an inspection device configured to detect bias in distribution of processing qualities of said at least one treatment object and determine a position of the detected bias on the at least one treatment object; and
an analyzing device configured to specify at least one processing device or one processing device group of the plurality of processing devices in which bias is detected based on the position of the detected bias on the at least one treatment object and the set positions for the at least one treatment object in each processing device.

2. The manufacturing inspection/analysis system of claim 1, wherein the analyzing device further includes a position change setting section that instructs the position change section of each of the plurality of processing devices of the set position.

3. The manufacturing inspection/analysis system of claim 2, wherein at least one of the plurality of processing devices includes:
a plurality of processing sections, each of the plurality of processing section configured to subject said at least one treatment object to the manufacturing process; and a transportation section configured to transport said at least one treatment object to the plurality of processing sections, and
on account of the transportation section, said at least one treatment object is transported to the respective processing sections from different directions, so that the position change section is realized.

4. The manufacturing inspection/analysis system as defined in claim 2, wherein,
said at least one treatment object is classified into processing groups, and
the position change setting section causes a combination of positions of those treatment objects in one processing group to be different among the processing devices or the processing device groups.

5. The manufacturing inspection/analysis system as defined in claim 4, wherein,
the position change setting section changes the combination, in accordance with a time period.

6. The manufacturing inspection/analysis system of claim 2, wherein
the position change section is configured to change positions of some of said at least one treatment object, which are stored in a treatment object transportation member.

7. The manufacturing inspection/analysis system of claim 1, wherein the inspection device is an appearance inspection device configured to detect the bias by inspecting appearance of said at least one treatment object.

8. The manufacturing inspection/analysis system of claim 1, wherein the inspection device is an electric property evaluation device configured to detect the bias by inspecting an electric property of said at least one treatment object.

9. The manufacturing inspection/analysis system of claim 1, wherein the position change section is configured to change the position of said at least one treatment object by rotating said at least one treatment object.

10. The manufacturing inspection/analysis system of claim 1, wherein the position change section is configured to change the position of said at least one treatment object by horizontally moving said at least one treatment object.

11. The manufacturing inspection/analysis system of claim 1, wherein
said at least one treatment object is a flat plate, and
the position change section is configured to change the position of said at least one treatment object by turning over said at least one treatment object.

12. The manufacturing inspection/analysis system of claim 1, wherein
the position change section is configured to change the position of said at least one treatment object outside a processing section of at least one of the plurality of processing devices.

13. The manufacturing inspection/analysis system of claim 1, wherein
the position change section is configured to change the position of said at least one treatment object inside a processing section of each of the plurality of processing devices.

14. The manufacturing inspection/analysis system of claim 1, wherein
the position change section is realized in each of the plurality of processing devices based on a positional relationship between a processing device and a directly preceding processing device, and
the position change section is configured to change the position of said at least one treatment object on account of transportation of the treatment object from the directly preceding processing device.

15. The manufacturing inspection/analysis system of claim 1, wherein said at least one treatment object is either one of a flat plate as a semiconductor wafer, a glass plate, and a resin plate.

16. The manufacturing inspection/analysis system of claim 1, wherein said at least one treatment object has a three-dimensional structure.

17. The manufacturing inspection/analysis system of claim 1, wherein each of the plurality of processing devices are at least one of: a film forming device, a heat treatment device, an injection device, an etching device, a polishing device, an applicator device, an exposing device, a developing device, a washing device, a cutting device, an adhesion device, a joining device, a film thickness measurement device, a line width measurement device, and an alignment checking device.

18. The manufacturing inspection/analysis system of claim 1, wherein at least one of the plurality of processing devices is a transportation device configured to transport said at least one treatment object from and/or to another processing device.

19. An analyzing device in a manufacturing inspection/analysis system, the analyzing device comprising: position change setting section configured to instruct a position change in each of a plurality of processing devices to change a position of the at least one treatment object to a set position, wherein the set position is different for each processing device or each processing device group; analyzing process section configured to receive positional information indicating the set positions for the at least one treatment object in each processing device and bias information indicating detection of bias in distribution of processing qualities of the at least one treatment object and position of the detected bias on the at least one treatment object, the analyzing process section configured to specify at least one processing device or one processing device group of the plurality of processing devices in which bias is detected based on the position of the detected bias on the at least one treatment object and the set positions for the at least one treatment object in each processing device.

20. A computer-readable storage medium storing a computer program for controlling an analyzing device, the computer program including executable instructions for causing a computer to execute an analysis process, comprising: instructing a position change section in each of a plurality of processing devices to change a position of at least one treatment object to a set position, wherein the set position is different for each processing device or each processing device group; receiving positional information indicating the set positions for the at least one treatment object in each processing device and bias information indicating detection of bias in distribution of processing qualities of the at least one treatment object and position of the detected bias on the at least one treatment object, specifying at least one processing device or one processing device group of the plurality of processing devices in which bias is detected based on the position of the detected bias on the at least one treatment object and the set positions for the at least one treatment object in each processing device.

21. A manufacturing inspection/analysis method, including: instructing a position change section in each of a plurality of processing devices to change a position of at least one treatment object to a set position, wherein the set position is different for each processing device or each processing device group; receiving positional information indicating the set positions for the at least one treatment object in each processing device and bias information indicating detection of bias in distribution of processing qualities of the at least one treatment object and position of the detected bias on the at least one treatment object, specifying at least one processing device or one processing device group of the plurality of processing devices in which bias is detected based on the position of the detected bias on the at least one treatment object and the set positions for the at least one treatment object in each processing device.

* * * * *